(12) United States Patent
Tomaney et al.

(10) Patent No.: US 10,605,737 B2
(45) Date of Patent: Mar. 31, 2020

(54) SIGNAL NOISE REDUCTION FOR IMAGING IN BIOLOGICAL ANALYSIS

(71) Applicant: APPLIED BIOSYSTEMS, LLC, Carlsbad, CA (US)

(72) Inventors: Austin B. Tomaney, Burlingame, CA (US); Mark F. Oldham, Emerald Hills, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 84 days.

(21) Appl. No.: 15/480,530

(22) Filed: Apr. 6, 2017

(65) Prior Publication Data

US 2017/0276609 A1 Sep. 28, 2017

Related U.S. Application Data

(60) Division of application No. 14/271,173, filed on May 6, 2014, now Pat. No. 9,651,495, which is a
(Continued)

(51) Int. Cl.

| | |
|---|---|
| *G01N 21/64* | (2006.01) |
| *H04N 5/361* | (2011.01) |
| *H04N 5/367* | (2011.01) |
| *H04N 5/225* | (2006.01) |
| *H04N 5/357* | (2011.01) |

(52) U.S. Cl.
CPC ..... *G01N 21/6486* (2013.01); *G01N 21/6428* (2013.01); *H04N 5/225* (2013.01); *H04N 5/357* (2013.01); *H04N 5/361* (2013.01); *H04N 5/367* (2013.01); *G01N 2201/062* (2013.01);
(Continued)

(58) Field of Classification Search
CPC .................................................. G01N 21/6486
See application file for complete search history.

(56) References Cited

U.S. PATENT DOCUMENTS

| | | | |
|---|---|---|---|
| 4,567,525 A | 1/1986 | Endo et al. | |
| 4,602,291 A | 7/1986 | Temes | |

(Continued)

FOREIGN PATENT DOCUMENTS

| | | |
|---|---|---|
| EP | 01378200 | 1/2004 |
| JP | 2011505676 | 5/1999 |

(Continued)

OTHER PUBLICATIONS

Lucas, R.A., Desjardins, T., et al., ACS Data Handbook v. 9.0, "Chapter 4.3: Dark Current, Hot Pixels, and Cosmic Rays," originally pub. 2001, rev. 2018 (Baltimore STScI); Retrieved from url <http:www.stci.edu/hst/acs/documents/handbooks/currentDHB/acs_Ch44.html>; Retrieved [Oct. 17, 2018]. (Year: 2018).*

(Continued)

*Primary Examiner* — Yara B Green
(74) *Attorney, Agent, or Firm* — Jones Robb, PLLC

(57) ABSTRACT

A system and method for characterizing contributions to signal noise associated with charge-coupled devices adapted for use in biological analysis. Dark current contribution, readout offset contribution, photo response non-uniformity, and spurious charge contribution can be determined by the methods of the present teachings and used for signal correction by systems of the present teachings.

13 Claims, 14 Drawing Sheets

Related U.S. Application Data continuation of application No. 14/160,376, filed on Jan. 21, 2014, now abandoned, which is a continuation of application No. 14/066,586, filed on Oct. 29, 2013, now abandoned, which is a continuation of application No. 13/931,643, filed on Jun. 28, 2013, now abandoned, which is a continuation of application No. 13/593,945, filed on Aug. 24, 2012, now Pat. No. 8,482,730, which is a continuation of application No. 12/775,391, filed on May 6, 2010, now Pat. No. 8,274,650, which is a continuation of application No. 12/220,763, filed on Jul. 28, 2008, now Pat. No. 7,715,004, which is a continuation of application No. 11/803,403, filed on May 14, 2007, now Pat. No. 7,405,823, which is a continuation of application No. 10/913,601, filed on Aug. 5, 2004, now Pat. No. 7,233,393.

(52) U.S. Cl.
CPC ........... *G01N 2201/06113* (2013.01); *G01N 2201/08* (2013.01); *G01N 2201/121* (2013.01)

(56) References Cited

U.S. PATENT DOCUMENTS

| | | | |
|---|---|---|---|
| 4,742,396 | A | 5/1988 | Bell |
| 5,552,824 | A | 9/1996 | DeAngelis et al. |
| 5,672,881 | A | 9/1997 | Striepeke et al. |
| 5,710,381 | A | 1/1998 | Atwood et al. |
| 5,818,973 | A | 10/1998 | Hsu |
| 5,838,372 | A | 11/1998 | Wood |
| 6,051,191 | A | 4/2000 | Ireland et al. |
| 6,208,749 | B1 | 3/2001 | Gutkowicz-Krusin et al. |
| 6,277,630 | B1 | 8/2001 | Brophy et al. |
| 6,340,589 | B1 | 1/2002 | Turner et al. |
| 6,419,638 | B1 | 7/2002 | Hay et al. |
| 6,457,861 | B1 * | 10/2002 | Petrick ............... A61B 6/032 378/207 |
| 6,518,068 | B1 | 2/2003 | Gambini et al. |
| 6,528,302 | B2 | 3/2003 | Turner et al. |
| 6,642,499 | B1 | 11/2003 | Boni et al. |
| 6,660,232 | B1 | 12/2003 | Krueger et al. |
| 6,669,911 | B1 | 12/2003 | Swanson |
| 6,818,437 | B1 | 11/2004 | Gambini et al. |
| 7,233,393 | B2 | 6/2007 | Tomaney et al. |
| 7,347,977 | B2 | 3/2008 | Gülzow et al. |
| 7,405,823 | B2 | 7/2008 | Tomaney et al. |
| 7,455,966 | B1 | 11/2008 | Schaudies et al. |
| 7,473,891 | B2 | 1/2009 | Sagatelyan |
| 7,715,004 | B2 | 5/2010 | Austin et al. |
| 7,759,636 | B2 | 7/2010 | Dmitry |
| 8,274,650 | B2 | 9/2012 | Tomaney et al. |
| 2003/0007146 | A1 | 1/2003 | Malczewski |
| 2003/0134807 | A1 | 7/2003 | Hardin |
| 2003/0179418 | A1 * | 9/2003 | Wengender ........... H04N 1/401 358/437 |
| 2003/0210344 | A1 | 11/2003 | Bloom |
| 2004/0002125 | A1 | 1/2004 | Gombrich |
| 2004/0051797 | A1 | 3/2004 | Kelly et al. |
| 2007/0246858 | A1 | 10/2007 | Gülzow et al. |
| 2008/0084004 | A1 | 4/2008 | Gülzow et al. |
| 2008/0290283 | A1 | 11/2008 | Austin et al. |
| 2011/0079705 | A1 | 4/2011 | Tomaney et al. |

FOREIGN PATENT DOCUMENTS

| | | |
|---|---|---|
| JP | 2003505691 | 3/2004 |
| JP | 2005079948 | 9/2009 |
| WO | 96/01022 | 1/1996 |
| WO | 2001/07896 | 2/2001 |

OTHER PUBLICATIONS

Vaghmare, K., "Tutorial: Basic Image Reduction with IRAF", Retrieved from url <https://vkaustubh.github.io/static/files/IRAF_BasicRed.pdf>, Retrieved [Oct. 17, 2018]; archived 2017. (Year: 2017).*
"Getting the Right CCD", Photonics Tech Briefs, Sep. 1999.
"Interlace Operation in TI Virtual CCD Image Sensors", Texas Instruments, Jan. 1993.
Davis, L.E., "A Reference Guide to the IRAF/DAOPHOT Package", NOAO Publication, 1994.
Des Jardin, Wiliam et al., "True Two-Phase CCD-Image Sensors Employing a Transparent Gate", Presented at Photonics West, Jan. 1999.
Djorgovski, S., "Proceedings of the Workshop on Improvements to Photometry", eds. W.J. Borucki & A. Young, NASA Conf. Pub 2350, 1984.
Gilliland, R., "Astronomical CCD observing and Reduction Techniques", ASP Conference Series vol. 23. Ed., S. Howell, 1992, p. 68.
Gullixson, C., "Astronomical CCD observing and Reduction Techniques", ASP Conference Series vol. 23. Ed., S. Howell, p. 130.
Hiraoka, Y., "http://www.msg.ucsf.edu/agard/Publications/14-Agard-Science-87.pdf", Science, vol. 238, 1987, p. 36.
Janesick, James R., "Scientific Charge-Coupled Devices", Chapter 6; Charge Measurement, 2001, 532-556.
Janesick, James R., "Scientific Charge-Coupled Devices", Chapter 7, Noise Sources, 2001, 605-720.
PCT/US2005/028066, Revised Version of International Search Report, dated Mar. 2, 2006.
PCT/US2005/028066, International Search Report and the Written Opinion, dated Mar. 2, 2006, 10 pgs.
PCT/US2005/028066, Notice of Transmittal of the International Search Report and the Written Opinion, dated Mar. 2, 2006, 3 pgs.
PCT/US2005/028066, International Search Report, dated Mar. 2, 2006, 4 pgs.
WO06/017810, Written Opinion, dated Mar. 2, 2006, 6 pgs.
Machine-generated English Translation of JP 2005-079948.

* cited by examiner

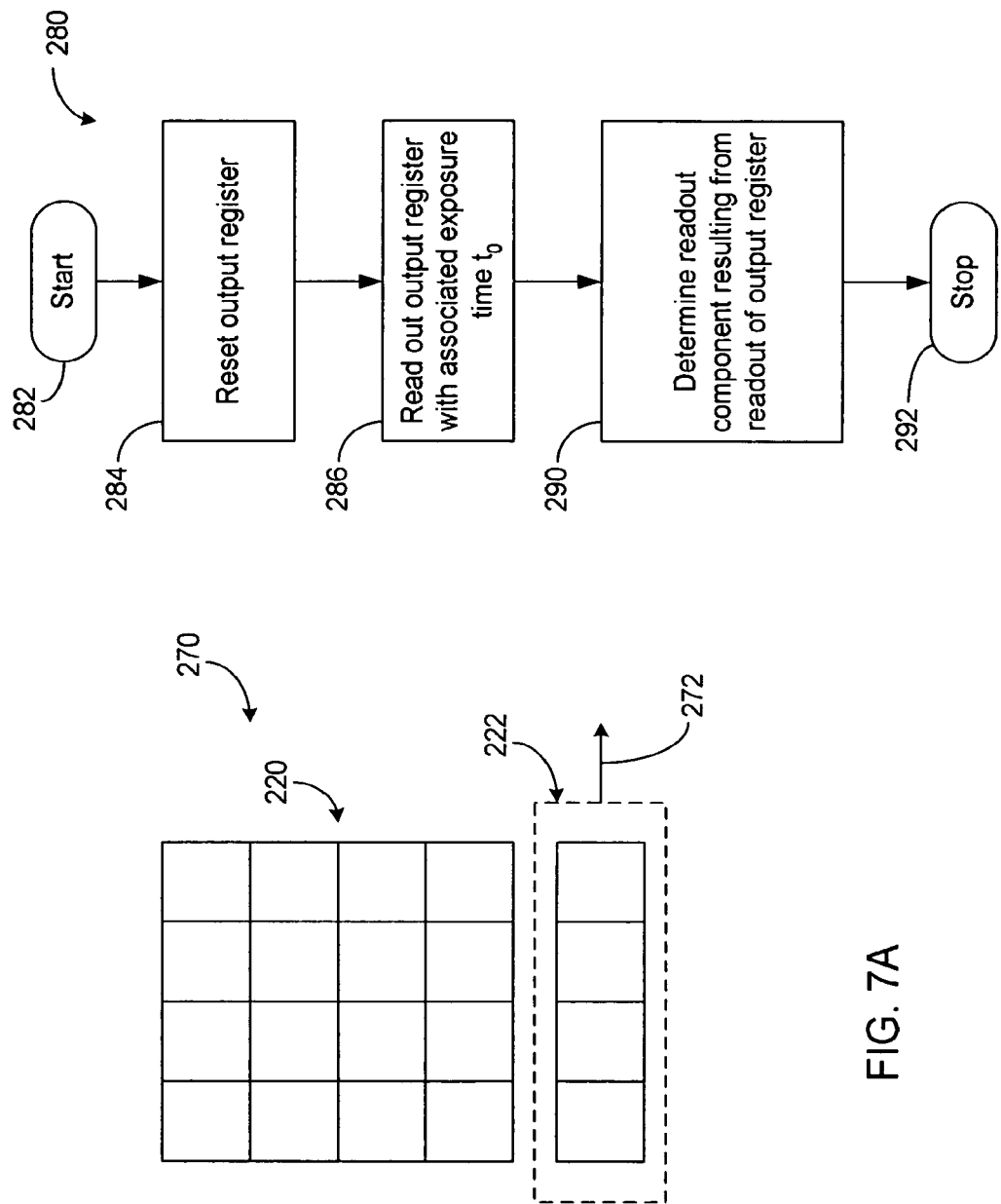

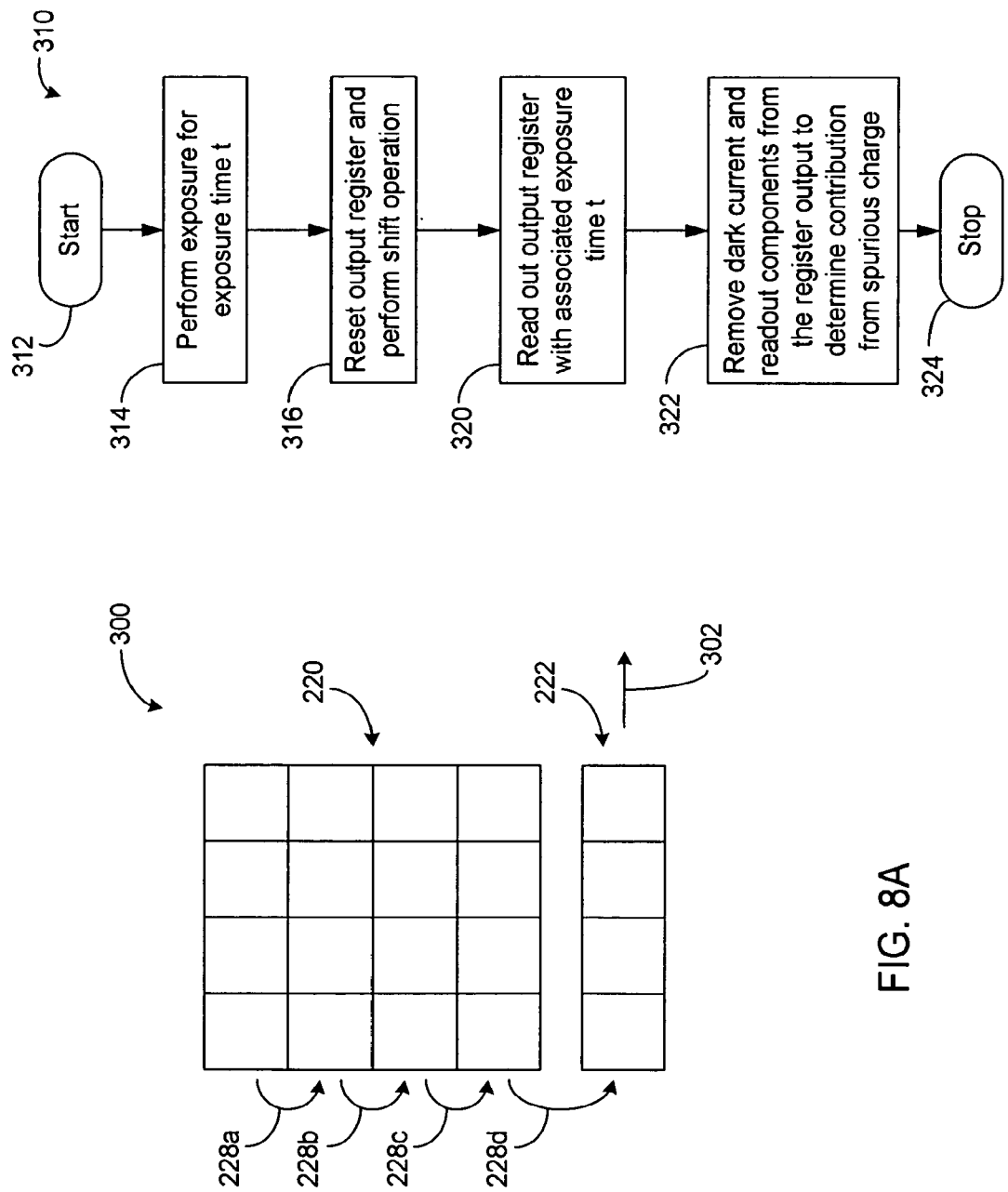

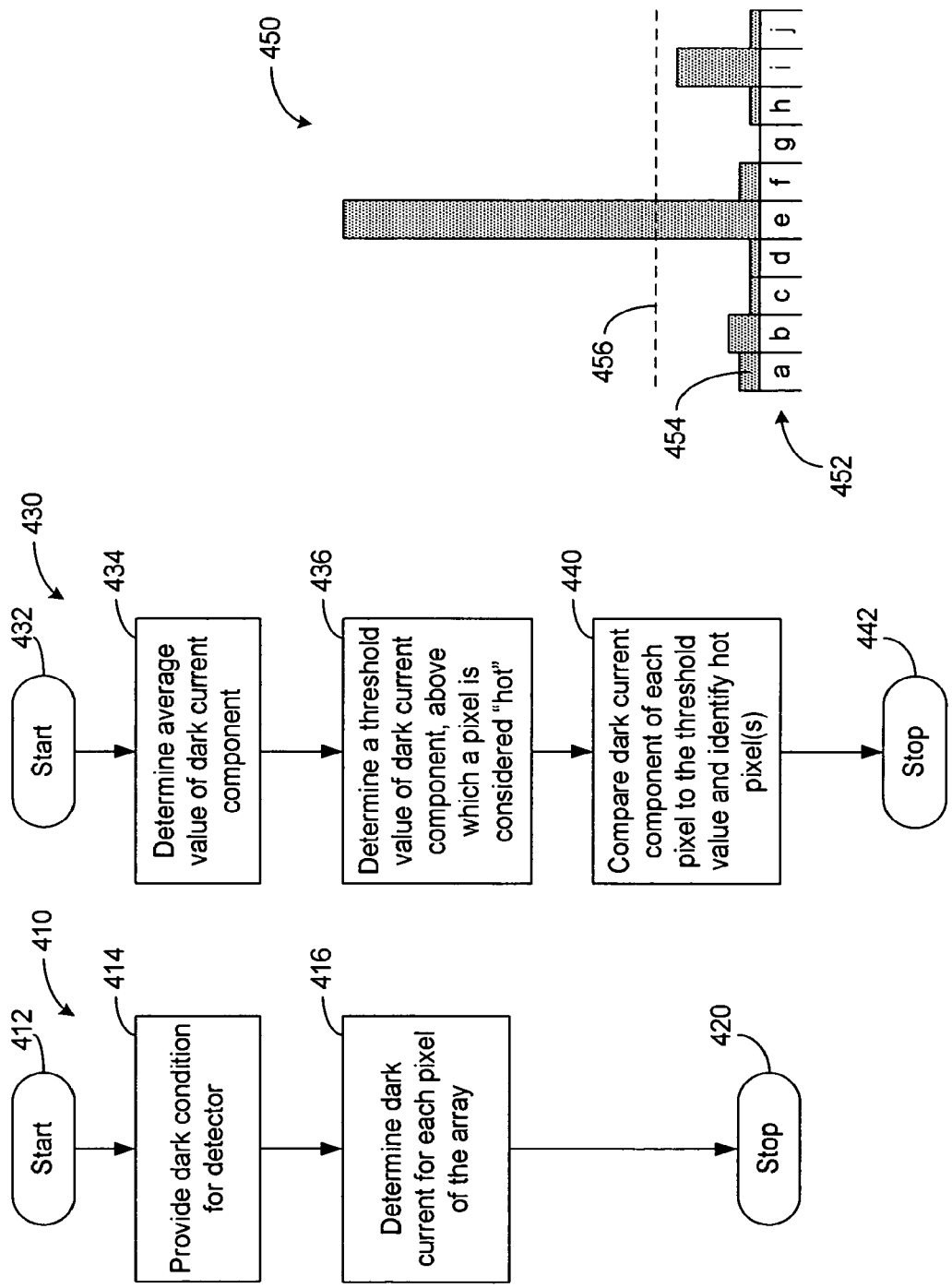

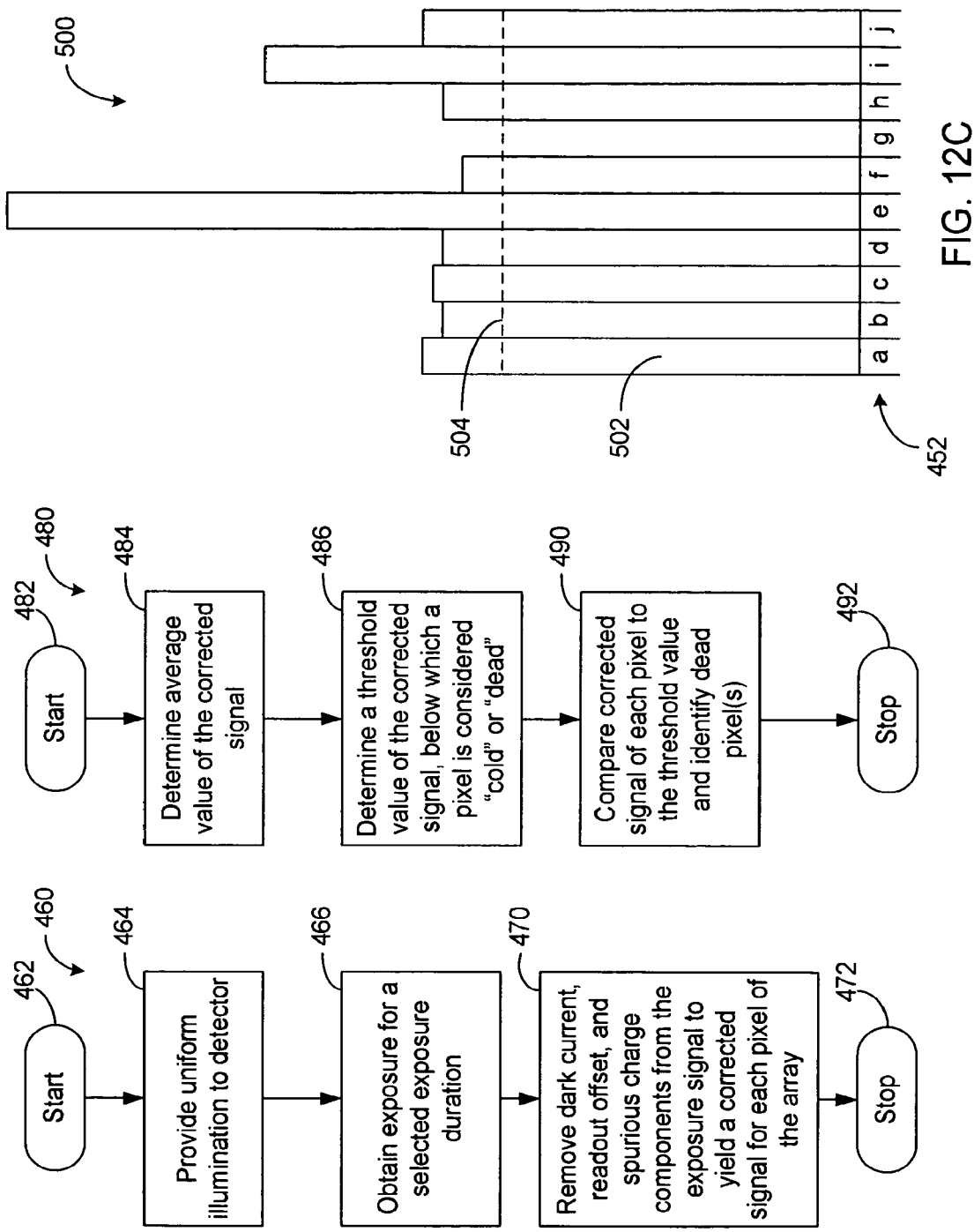

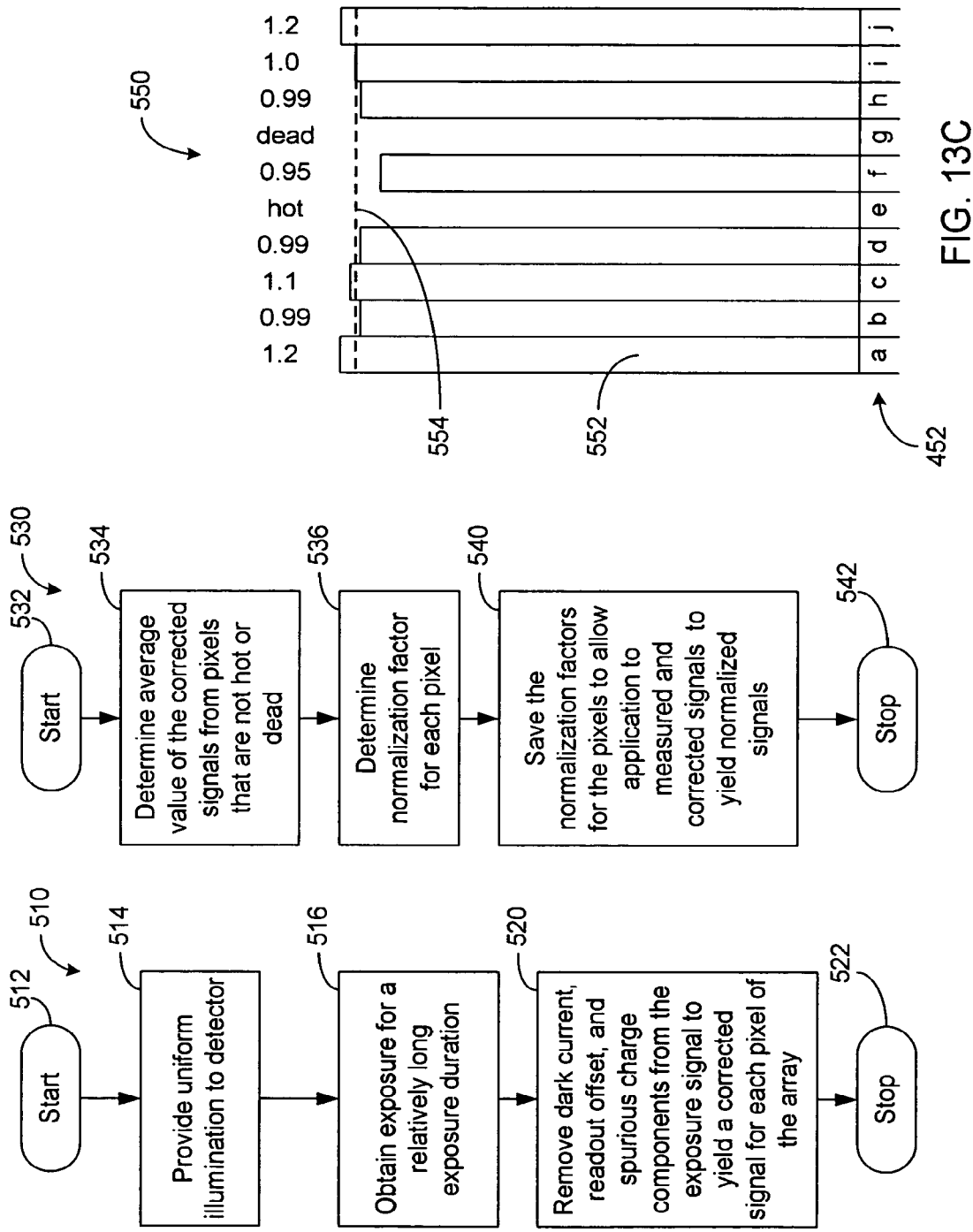

SIGNAL NOISE REDUCTION FOR IMAGING IN BIOLOGICAL ANALYSIS

CROSS-REFERENCE TO RELATED APPLICATION

This application is a Divisional Application of U.S. patent application Ser. No. 14/271,173, filed May 6, 2014, which is a Continuation Application of U.S. patent application Ser. No. 14/160,376, filed Jan. 21, 2014 (now abandoned), which is a Continuation Application of U.S. patent application Ser. No. 14/066,586, filed Oct. 29, 2013 (now abandoned), which is a Continuation Application of U.S. patent application Ser. No. 13/931,643, filed Jun. 28, 2013 (now abandoned), which is a Continuation Application of U.S. patent application Ser. No. 13/593,945, filed Aug. 24, 2012 (now U.S. Pat. No. 8,482,730), which is a Continuation Application of U.S. patent application Ser. No. 12/775,391, filed May 6, 2010 (now U.S. Pat. No. 8,274,650), which is a Continuation Application of U.S. patent application Ser. No. 12/220,763, filed Jul. 28, 2008 (now U.S. Pat. No. 7,715,004), which is a Continuation Application of U.S. patent application Ser. No. 11/803,403, filed May 14, 2007 (now U.S. Pat. No. 7,405,823 B2), which is a Continuation Application of U.S. patent application Ser. No. 10/913,601, filed Aug. 5, 2004 (now U.S. Pat. No. 7,233,393 B2), which disclosures are herein incorporated by reference in their entirety.

FIELD

The present teachings generally relate to the field of signal processing and more particularly, to a system and methods for characterizing and correcting for noise contributions associated with signal imaging in biological analysis.

INTRODUCTION

During biological analysis, such as nucleotide sequencing, microarray processing, sequence detection, or high-throughput screening, photo-detectors such as charge coupled devices (CCD) can be used to detect signals arising from labeled samples or probe features responsive to selected target analytes. These signals can take the form of fluorescent or visible light emissions that are desirably analyzed to quantify signal intensities arising from each labeled sample or probe feature and are subsequently resolved to quantitatively or qualitatively evaluate the presence of a target analyte within a sample.

Generally, a CCD used in such a biological analysis includes an array of signal detecting pixels. The signal detection for a given pixel can be characterized as a conversion of an incident electromagnetic energy signal into a number of electron-hole pairs. The pixel can be configured to collect either the electrons or the holes thus generated with the number of collected charges representative of the incident energy. A CCD having a plurality of such pixels with collected charges can be read out by a sequence of shifting operations by applying a sequence of gate voltages to the pixels in a predetermined manner. The charge collected from a selected pixel can then be read out or quantitated and used for further analysis.

The operation of the CCD in the foregoing manner results in several undesirable effects that can be referred to collectively as "signal noise." Noise can include various contributions, and if not accounted for, generally degrades the quality of signal acquisition and can detrimentally affect the biological analysis. Consequently, there is an ongoing need for an improved approach to signal acquisition by photo detectors used in biological analysis systems.

SUMMARY

In various embodiments, the present teachings can provide a system for detecting one or more identifiable signals associated with one or more biological samples, the system including a segmented detector including a plurality of pixels that are capable of forming an optical image of fluorescent light emitted from the biological samples, a readout component that is capable of reading an output signal from each pixel, wherein the output signal includes a charge collected and transferred from the pixel, and wherein the readout component includes an output register that receives transferred charges from the plurality of pixels for readout, a controller that is capable of correcting signal noise from the output signal, wherein signal noise includes a dark current contribution and a readout offset contribution, and a processor capable of determining the dark current contribution and the readout offset contribution.

In various embodiments, the present teachings can provide a method for reducing signal noise from an array of pixels of a segmented detector for biological samples, wherein the signal noise includes a dark current contribution and readout offset contribution, the method including providing a substantially dark condition for the array of pixels, wherein the dark condition includes being substantially free of fluorescent light emitted from the biological samples, providing a first output signal from a binned portion of the array of pixels by collecting charge for a first exposure duration, transferring the collected charge to an output register and reading out the register, wherein transferring of the collected charge from the binned pixels includes providing a gate voltage to a region near the binned pixels to move the collected charge from the binned pixels, and wherein the collected charge is transferred in a manner that causes the collected charge to be shifted to the output register, providing a second output signal from each pixel by collecting charge for a second exposure duration, transferring the collected charge to the output register, and reading out the register, providing a third output signal by resetting and reading out the output register, determining the dark current contribution and the readout offset contribution from the first output signal, the second output signal, and the third output signal.

In various embodiments, the present teachings can provide a method of characterizing signal noise associated with operation of a charge-coupled device (CCD) adapted for analysis of biological samples, wherein the signal noise includes a dark current contribution, readout offset contribution, and spurious change contribution, the method including providing a plurality of first data points associated with first outputs provided from the CCD under a substantially dark condition during a first exposure duration, providing a plurality of second data points associated with second outputs provided from the CCD under the substantially dark condition during a second exposure duration wherein the second duration is different from the first duration, providing a plurality of third data points associated with third outputs provided from a cleared output register of the CCD without having charge transferred thereto, determining the dark current contribution per unit exposure time by comparing the first data points and the second data points, determining the readout offset contribution from the third data points, and determining the spurious charge contribution based on the dark current contribution and the readout offset contribution.

BRIEF DESCRIPTION OF THE DRAWINGS

FIGS. 7A and 7B illustrate a method for determining a readout offset contribution of noise associated with the operation of the pixels according to the present teachings;

FIGS. 8A and 8B illustrate a method for determining a spurious charge contribution of the noise associated with the operation of the pixels according to the present teachings;

FIGS. 11A-11C illustrate an application of the pixels' noise contributions characterization to identify hot pixels according to the present teachings;

FIGS. 12A-12C illustrate an application of the pixels' noise contributions characterization to identify cold or dead pixels according to the present teachings;

FIGS. 13A-13C illustrate an application of the pixels' noise contributions characterization to normalize the responses of the pixels according to the present teachings.

DESCRIPTION OF VARIOUS EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components having one unit and elements and components that having more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose. In the event that one or more of the incorporated literature and similar materials differs from or contradicts this application, including but not limited to defined terms, term usage, described techniques, or the like, this application controls.

The term "fluorescent" as used herein refers to light emitted by a biological sample whether by fluorescence or chemiluminescence.

The term "biological sample" or "biological analysis" as used herein refers to a material and processes related to nucleic acids as known in the biological arts.

Figure 1A:
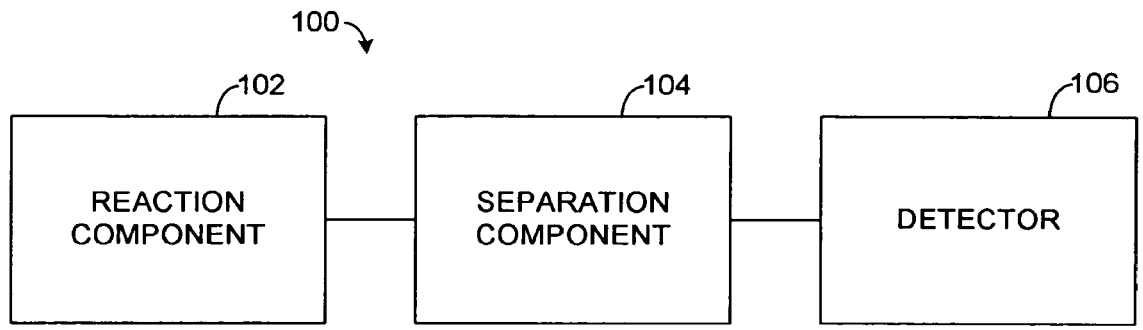
FIG. 1A illustrates a functional block diagram of a system adapted to measure components associated with biological related processes according to the present teachings.

FIG. 1A illustrates an exemplary schematic diagram for a biological analyzer 100 capable of sequence determination or fragment analysis for nucleic acid samples and other applications. In various embodiments, the analyzer 100 can include one or more components or devices that are used for labeling and identification of the sample and can perform automated sequence analysis. The various components of the controller can include separate components or a singular integrated system. It will be appreciated that the present teachings can be applied to both automatic and semi-automatic sequence analysis systems as well as to methodologies wherein some of the sequence analysis operations are manually performed. Additionally, the methods described herein can be applied to other biological analysis platforms to improve the overall quality of the analysis.

In various embodiments, the methods and systems of the present teachings can be applied to numerous different types and classes of photo and signal detection methodologies and are not necessarily limited to CCD-based detectors. The present teachings describe various embodiments for sequence analysis and for other biological analysis where signal noise reduction can provide detection of smaller quantities of fluorescent light emitted from locations that are in closer proximity.

It will also be appreciated that the methods and systems of the present teachings can be applied to photo-detectors in these applications. Photo-detectors in general convert incident photons to electrical signals, and can include, by way example, CCDs, CMOS devices, photomultipliers, or other semiconductor based devices such as photo-diodes.

In the context of sequence analysis, the exemplary sequence analyzer 100 can include a reaction component 102 wherein amplification or reaction sequencing (for example, through label or marker incorporation by polymerase chain reaction) of various constituent molecules contained in the sample is performed. Using these amplification techniques, a label or tag, such as a fluorescent or radioactive dideoxy-nucleotide can be introduced into the sample constituents resulting in the production of a collection of nucleotide fragments of varying sequence lengths. Additionally, one or more labels or tags can be used during the amplification step to generate distinguishable fragment populations for each base/nucleotide to be subsequently identified. Following amplification, the labeled fragments can then be subjected to a separation operation using a separation component 104. In one aspect, the separation component 104 includes a gel-based or capillary electrophoresis apparatus which resolves the fragments into substantially discrete populations. Using this approach, electrical current can be passed through the labeled sample fragments which have been loaded into a separation matrix (e.g. polyacrylamide or agarose gel). The application of an electrical current results in the migration of the sample through the matrix. As the sample migration progresses, the labeled fragments are separated and passed through a detector 106 wherein resolution of the labeled fragments is performed.

In one aspect, the detector 106 can identify various sizes or differential compositions for the fragments based on the presence of the incorporated label or tag. In one exemplary embodiment, fragment detection can be performed by generation of a detectable signal produced by a fluorescent label that is excited by a laser tuned to the label's absorption wavelength. Energy absorbed by the label results in a fluorescence emission that corresponds to a signal measured for each fragment. By keeping track of the order of fluorescent signal appearance along with the type of label incorporated into the fragment, the sequence of the sample can be discerned. A more detailed explanation of the sequencing process is provided in commonly assigned U.S. Pat. No. 6,040,586, entitled "Method and System for Velocity-Normalized Position-Based Scanning."

Figure 1B:
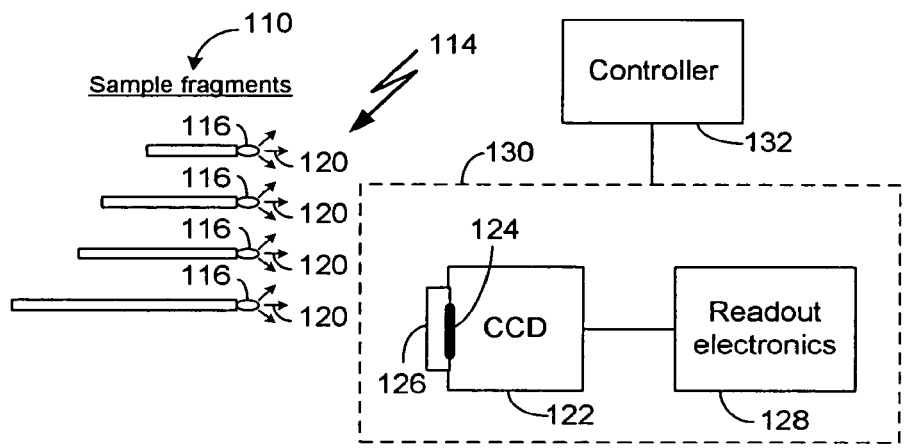
FIGS. 1B and 1C illustrate example biological analysis systems that utilize CCDs to detect signals from samples adapted to emit electromagnetic energy in a selected manner according to the present teachings.

FIG. 1B illustrates exemplary components for a detector 130 which can be used to acquire the signal associated with a plurality of labeled fragments 110. As previously indicated, the labeled fragments 110 can be resolved by measuring the quantity of fluorescence or emitted energy generated when the fragments 110 are subjected to an excitation 114 of the appropriate wavelength and energy that can be provided by a source such as an LED or tuned laser. The energy emissions 120 produced by a label 116 associated with the fragments 110 can be detected using a charge-coupled device (CCD) 122 as the fragments 110 pass through a detection window 126 wherein a plurality of energy detecting elements (e.g., pixels) 124 capture at least a portion of the emitted energy from the label 116. In one aspect, an electronic signal is generated by the CCD 122 that is approximately proportional to the relative abundance of the fragments 110 passing through the detection window 126 at the time of energy capture and the order which the fragments 110 appear in the detection window 126 can be indicative of their relative length with respect to one another based on certain sequencing or fragment analysis schemes.

In various embodiments, readout component 128 can provide electronics assembly configured to perform readout operations to acquire the electronic signal generated by the CCD 122 in response to the fragments 110. In various embodiments, some of the information that can be determined through signal readout and subsequent resolution and peak identification can include determination of the relative abundance or quantity of each fragment population. Evaluation of the signals can further be used to determine the sequence or composition of the sample using various known base sequence resolution techniques. It will further be appreciated by one of skill in the art that the exemplified signal distribution can represent one or more nucleic acid fragments for which the relative abundance of each fragment can be evaluated based, in part, upon the determination of the relative area of an associated peak in the signal distribution. The present teachings can therefore be integrated into existing analysis approaches to facilitate peak evaluation and subsequent integration operations typically associated with sequence analysis.

In various embodiments, the readout of the signal from the CCD 122 and selected control of the CCD 122 can be advantageously performed by controller 132. The controller 132 can be configured to operate in conjunction with one or more processors and/or one or more other controllers. Such controller and processor's components can include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the controller 132 can output a processed signal or analysis results to other devices or instrumentation where further processing can take place.

Figure 1C:
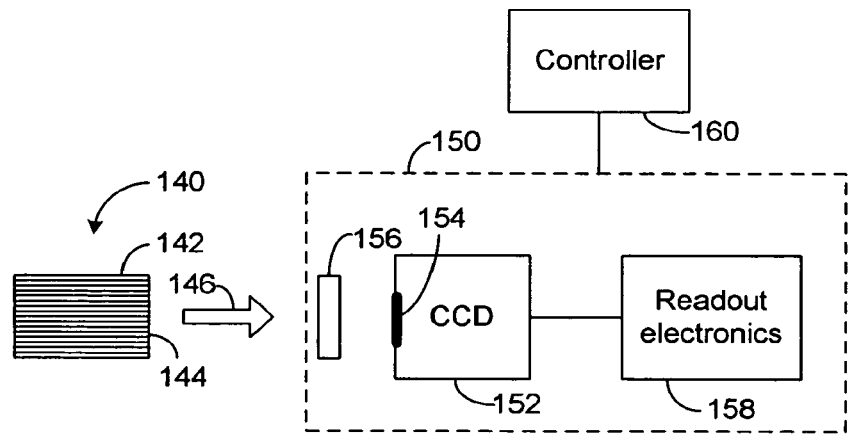

FIG. 1C illustrates another configuration of exemplary components for a detector 150 which can be used to acquire the signals associated with a plurality of labeled fragments forming an array, microarray, or biochip assay. One exemplary configuration of an array used in biological analysis can include a plurality of labeled fragments configured to adhere selectively to an array of tips 144 of a plurality of fibers 142. Such an array type of sample platform 140 can be utilized to simultaneously characterize concentrations of different types of fragments present in a sample. As previously indicated, the labeled fragments attached to the fiber tips 144 can be resolved by measuring the quantity of fluorescence or emitted energy generated when the fragments are subjected to an excitation source of the appropriate wavelength and energy from an excitation light source. The energy emissions 146 produced by a label associated with the fragments can be detected using a charge-coupled device (CCD) 152 via some form of optics 156, wherein a plurality of energy detecting elements (e.g., pixels) 154 capture at least a portion of the emitted energy from the labeled fragments. In one aspect, an electronic signal is generated by the CCD 152 that is approximately proportional to the relative abundance of the fragments in the sample being measured. In various embodiments, readout component 158 can provide electronics assembly configured to perform readout operations to acquire the electronic signal generated by the CCD 152 in response to the fragments. In various embodiments, some of the information that can be determined through signal readout and subsequent resolution and peak identification can include determination of the relative abundance or quantity of each fragment population. The spatial resolution of the detected signal allows determination of the position on the sample platform from which the signal was emitted. Thus, by identifying the type of a fiber associated with that position, one can determine the type of fragments attached thereto. Such information facilitates determination of the sequence or composition of the sample using various known base sequence resolution techniques. It will further be appreciated by one of skill in the art that the exemplified signal distribution can represent one or more nucleic acid fragments for which the relative abundance of each fragment can be evaluated based, in part, upon the determination of the relative area of an associated peak in the signal distribution. The present teachings can therefore be integrated into existing analysis approaches to facilitate peak evaluation and subsequent integration operations typically associated with sequence analysis. It will also be understood that similar techniques can be implemented in other types of analysis.

In various embodiments, the readout of the signal from the CCD 152 and selected control of the CCD 152 can be advantageously performed by a controller 160. The controller 160 can be configured to operate in conjunction with one or more processors and/or one or more other controllers. Such controller and processor's components can include, but are not limited to, software or hardware components, modules such as software modules, object-oriented software components, class components and task components, processes methods, functions, attributes, procedures, subroutines, segments of program code, scripts, drivers, firmware, microcode, circuitry, data, databases, data structures, tables, arrays, and variables. Furthermore, the controller 160 can output a processed signal or analysis results to other devices or instrumentation where further processing can take place.

In various embodiments, some of the information that can be determined through signal (from feature) resolution and peak identification can include determination of the relative abundance or quantity of each fragment population. Evaluation of the signals can further be used to determine the sequence or composition of the sample using various known base sequence resolution techniques. It will further be appreciated by one of skill in the art that the exemplified signal distribution can represent one or more nucleic acid fragments for which the relative abundance of each fragment can be evaluated based, in part, upon the determination of the relative area of an associated peak in the signal distribution. The present teachings can therefore be integrated into existing analysis approaches to facilitate peak evaluation and subsequent integration operations typically associated with sequence analysis. It will also be understood that similar techniques can be implemented in other types of biological analysis.

Figure 2:
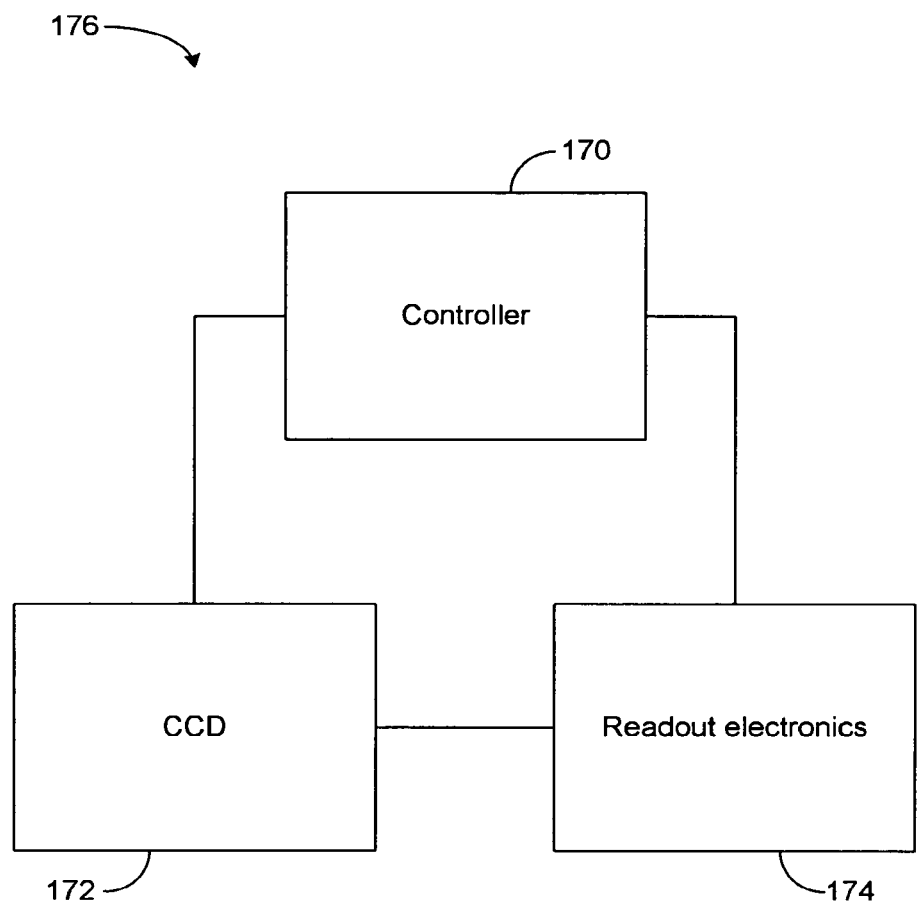
FIG. 2 illustrates one embodiment of a CCD readout control system according to the present teachings.

FIG. 2 now illustrates one embodiment of a detector control system 176 configured to facilitate the exemplary analysis systems described above. The detector control system 176 includes a controller 170 functionally coupled to a detector 172 and/or a readout electronic assembly 174. The detector control system 176 can be implemented in the exemplary biological analysis systems of FIGS. 1B and 1C, or any other suitable system. Thus, the detector 172 can represent the exemplary CCDs 122 and 152 (FIGS. 1B and 1C). Similarly, the readout assembly 174 can represent the exemplary readout electronics 128 and 158.

In one aspect, the present teachings relate to the controller manipulating the CCD 172 and/or the readout 174 in selected manners to characterize various components of a CCD signal that are commonly referred to as "signal noise." By identifying the noise associated with the CCD signal, it can be reduced in subsequent processing and signal resolution, thereby improving the CCD signal's signal-to-noise (S/N) ratio. In various embodiments, such improvements in the S/N ratio can facilitate more precise measurement of signals during biological analysis. For example, increasing the S/N ratio can facilitate detection and resolution of a fainter signal from a fluorescing DNA fragment type that is present in a relatively low concentrations or abundance.

In some embodiments, such manipulation of the CCD and/or readout can be achieved by controlling voltages associated. The voltages can be changed image to image. The voltages can also be changed within an image to trade off one or more performance parameters to reduce noise. For example, the readout speed can be slowed for an area of the detector where there is a region of interest.

As previously described in context of the exemplary sample analysis systems of FIGS. 1B and 1C, it will be appreciated that the controller 170 can be configured to operate in conjunction with one or more processors and/or one or more other controllers. Such controller and processor's components can include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the controller 170 can output a processed signal or analysis results to other devices or instrumentation where further processing can take place.

Figure 3A:
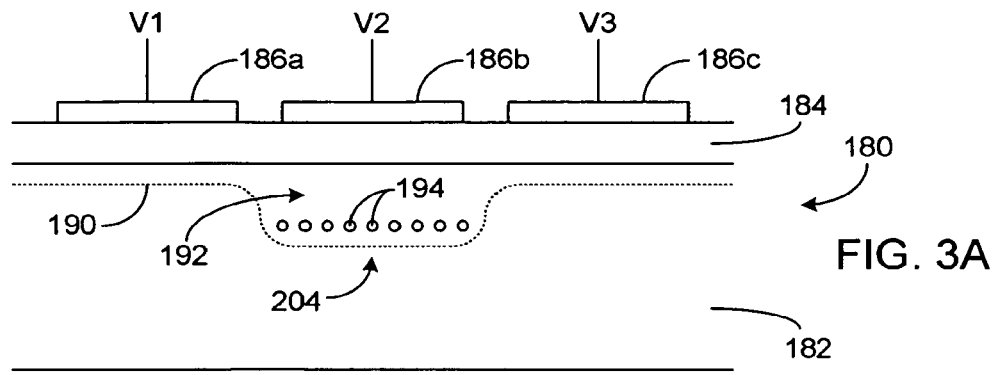
FIGS. 3A and 3B illustrate one embodiment of charge collection and charge transfer configurations for a pixel according to the present teachings.
Figure 3B:
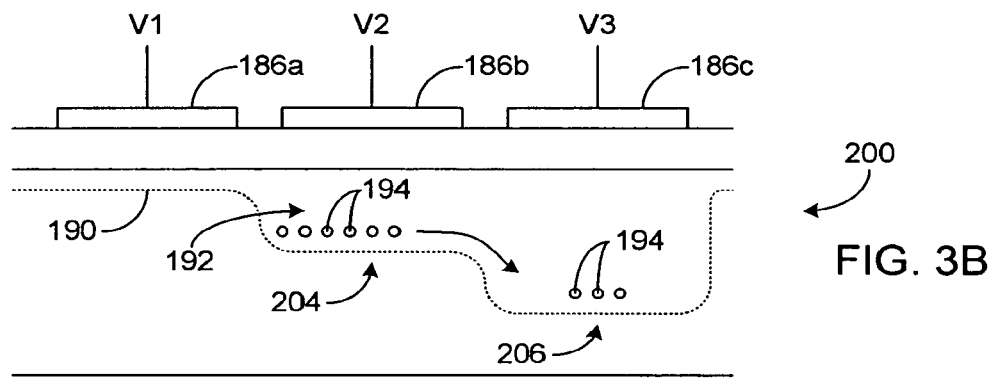

FIGS. 3A and 3B illustrate an exemplary operation of an exemplary CCD pixel. Such a pixel can be used in the CCD 172 described above in reference to FIG. 2. It will be appreciated that the depicted operation of the CCD is exemplary only, and the concepts disclosed herein can be implemented on other functional and/or operational types of CCDs without departing from the spirit of the present teachings.

As shown in FIGS. 3A and 3B, the exemplary pixel includes a substrate 182 and a storage region 192. An oxide layer 184 separates the substrate 182 from a plurality of gates 186a-186c that facilitate application of gate voltages to their corresponding regions in the substrate 182 and the storage region 192.

FIG. 3A depicts an exemplary storage configuration 180 that can be achieved when the gate voltages V1, V2, and V3 are selected such that a potential profile 190 forms a well 204. In certain embodiments, the gate voltages V1-V3 are held at a same level, and the presence of the storage region 192 forms the potential well 204. Charge 194 generated from the impinging signal(s) are thus collected in the well 204 until they are ready to be transferred out. It will be appreciated that for the purpose of description, the "charge" can represent electrons or holes. The substrate 182 and the storage region 192 can be configured in any number of ways by using various known techniques.

FIG. 3B illustrates an exemplary charge transfer configuration 200 wherein voltage V3 on the gate 186c is applied such that the potential profile 190 includes an inverted region 206 substantially adjacent the well. The potential of the inverted region 206 promotes the charge 194 to transfer from the well 192, depicted as being "lower" in the exemplary potential profile 190. The manipulation of the potential profile 190 thus allows the collected charge 194 to "shift" from the region adjacent the gate 186b to the region adjacent the gate 186c. Collected charge from the adjacent pixel (not shown) can also have been shifted in a similar manner, thereby allowing the charge 194 to temporarily occupy the adjacent pixel in the transfer process.

Figure 4:
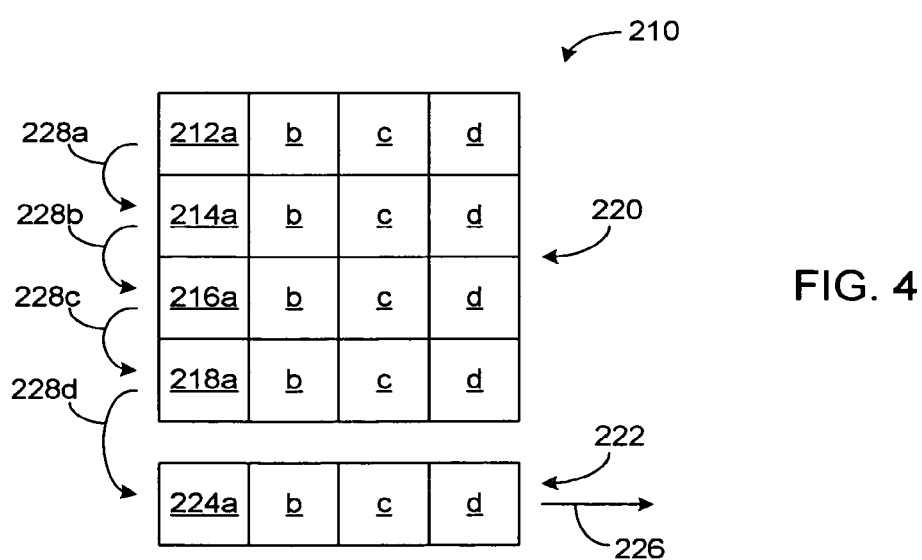
FIG. 4 illustrates one embodiment of a pixel array read out by pixel charge shifting according to the present teachings.

Such transfer of charges from a two dimensional exemplary array 210 of pixels is illustrated in FIG. 4. The exemplary array 210 is depicted as a 4×4 array having a pixel array 220 and an output register 222. The exemplary pixel array 220 includes four rows of four pixels 212a-212d, 214a-214d, 216a-216d, and 218a-218d. The exemplary output register 222 includes one row of four register elements 224a-224d.

During an exemplary readout operation, the charges stored in the pixels are shifted vertically (shown in the depiction of FIG. 4) such that row 218 charges are shifted to the output row 224 (as depicted by an arrow 228d), row 216 charges are shifted to the row 218 pixels (as depicted by an arrow 228c), and so on. When the charges from row 218 are shifted into the output row 224, they can read out from the readout register 222 by being shifted horizontally (shown in the depiction of FIG. 4). The readout of the output register 222 is depicted as an arrow 226. Thus, by transferring the collected charges in the pixels in a series of orchestrated shifts, the magnitudes of the charges originally collected in their corresponding pixels can be generally preserved and determined during the readout process.

As is understood in the art, the process of collecting charge in a given pixel, reading out of the charge from the pixel in the foregoing manner, and subsequent processing of the read out charge introduces at least some "noise" to the collected charge representative of the impinging signal that in turn is representative of the biological sample being measured. The noise can include different contributions, including but not limited to, a dark current contribution, spurious charge contribution, and readout offset contribution.

Dark current generally includes spontaneously generated charge, (for example, arising from thermal electrons) while the pixel is being operated (including integration or exposure operations). The dark current is generated whether or not the pixel is subjected to light, and is generally proportional to the duration of the integration (exposure).

In some embodiments, the amount of dark current can vary across the array if the readout time is large relative to the integration time. Thus, being able to manipulate different parts of the array can increase the overall performance of the detector.

Spurious charge can arise during the application of the gate voltage. This effect can be manifested particularly near the edges of the gate, and some of such generated charge can migrate and become part of the collected charge being transferred. Thus, spurious charge can contribute to the noise during the shifting operation described above in reference to FIGS. 3B and 4. The magnitude of the spurious charge can further depend on the gate voltage magnitude and/or its duration. In some embodiments, such magnitude depends particularly on whether the pixel is part of an electron multiplying register.

Readout offset generally results during the processing of the charge read out from the pixels. As an example, conversion of the analog (charge) signal to a digital representation via an ADC (analog-to-digital converter) typically introduces an offset. Similar to the dark current, such an offset is present whether or not the pixel is subjected to light.

Figure 5:
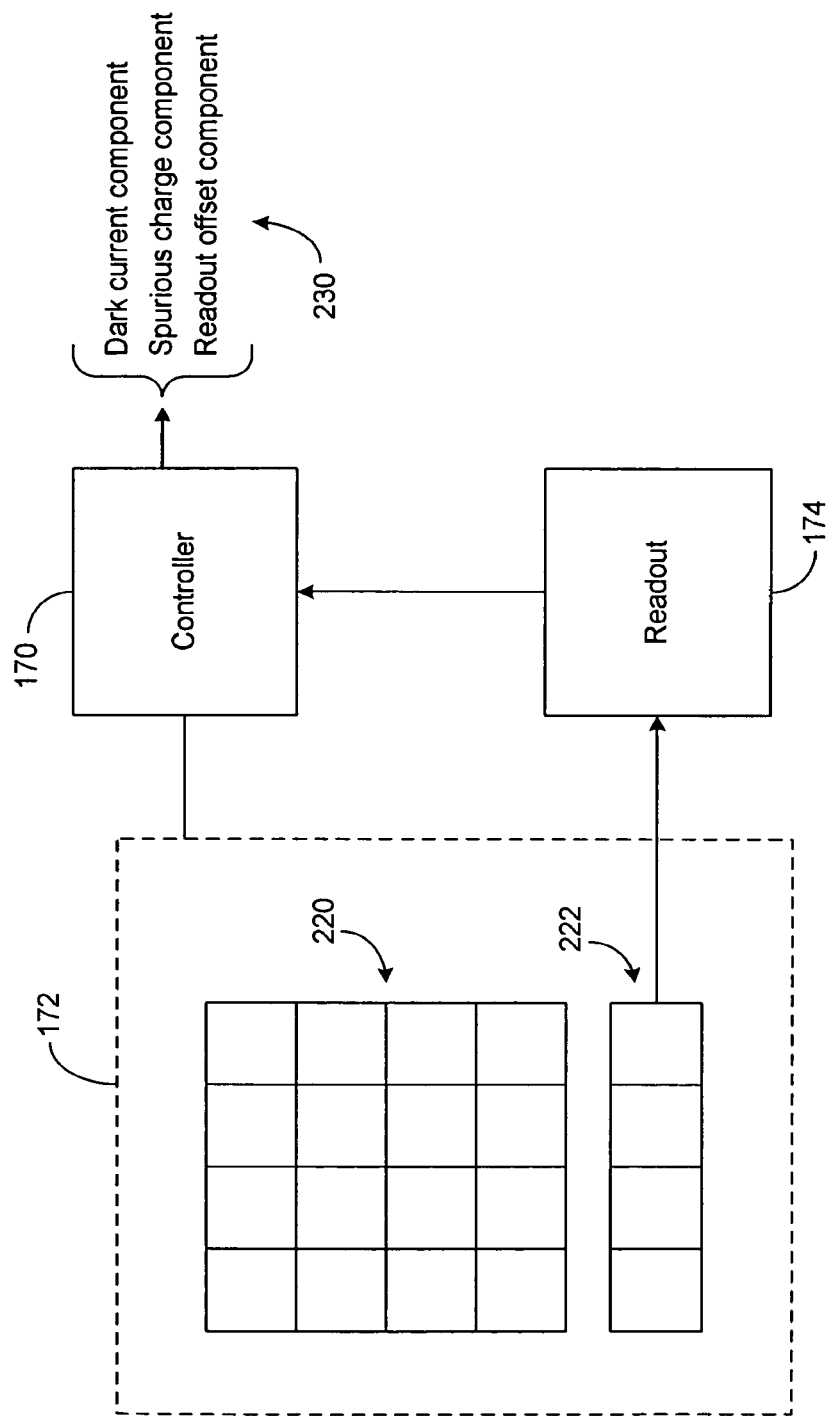
FIG. 5 illustrates one embodiment of a readout control system that allows characterization of various contributions of noise associated with the operation of the pixels according to the present teachings.

As illustrated in FIG. 5, one aspect of the present teachings relates to the controller 170 configured to interact with the CCD 172 and/or the readout 174 to characterize various contributions 230 of noise that affect the signal representative of the biological sample being measured. As previously described, the contributions 230 of the noise can include the dark current, spurious charge, and readout offset.

Figure 6B:
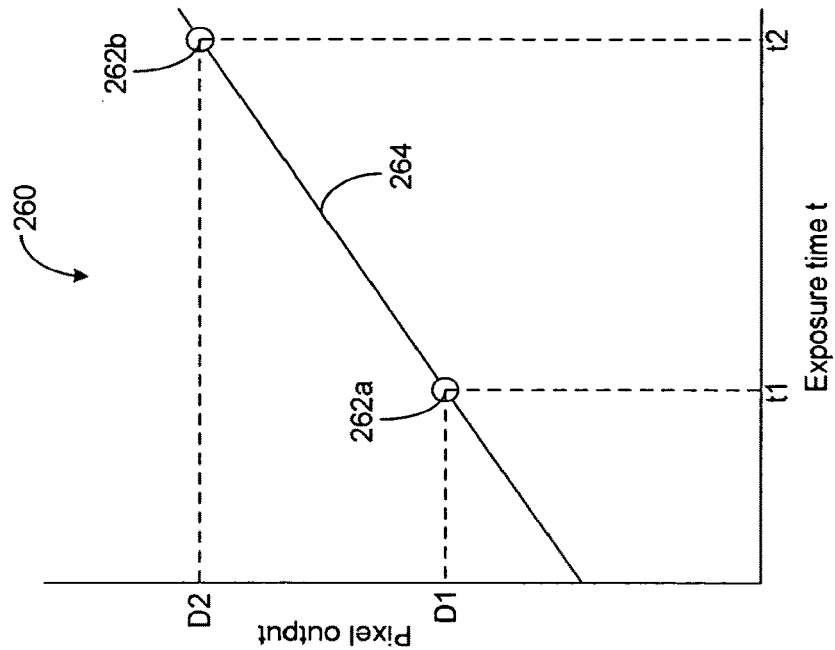
FIGS. 6A and 6B illustrate a method for determining a dark current contribution of noise associated with the operation of the pixels according to the present teachings.
Figure 6A:
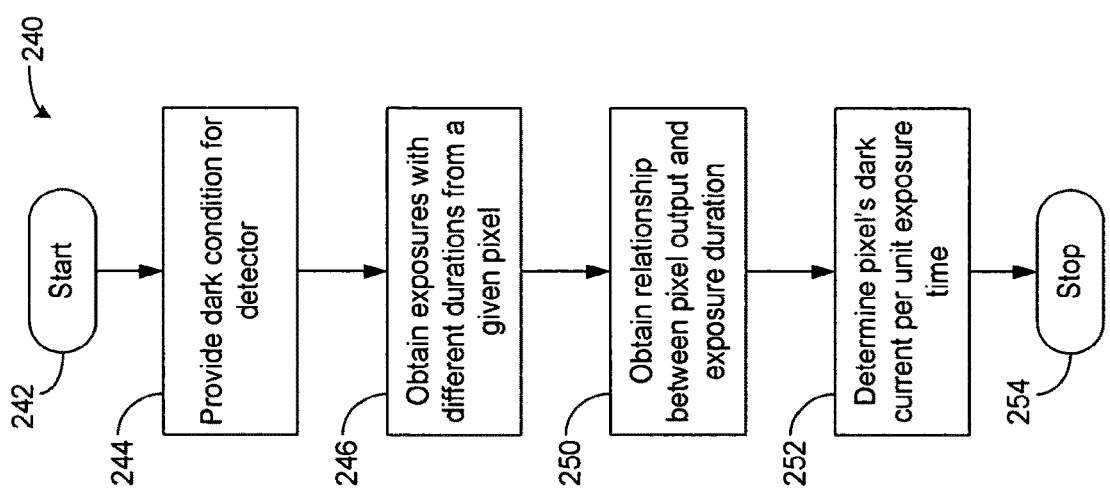

FIGS. 6A and 6B illustrate one possible manner of determining the dark current contribution associated with a given pixel. A process 240 that determines the dark current can be performed for each of the plurality of pixels of the CCD. The process 240 begins at a start state 242, and in step 244 that follows, the process 240 induces a dark condition to be applied to the detector. In step 246 that follows, the process 240 provides two or more exposures with different durations from the pixel. For the purpose of description, two such exposures are used. It will be appreciated, however, that more than two exposures can be used without departing from the spirit of the present teachings. In step 250 that follows, the process 240 provides a relationship between the pixel output and the exposure duration. Such a relationship can be provided from the two exposures in a manner described below in reference to FIG. 6B. In step 252 that follows, the process 240 determines the pixel's dark current per unit exposure time. The process 240 ends at a stop state 254.

In some embodiments, the dark current can also be determined from a masked area of a device. A number of exposures can be provided and averaged to improve the signal-to-noise ratio in determining the dark current.

FIG. 6B illustrates a graphical representation 260 of a relationship between the pixel output and the exposure duration (time). A first data point 262a corresponds to a first pixel output D1 provided from a dark exposure lasting for a first duration t1, and a second data point 262b corresponds to a second pixel output D2 provided from a dark exposure lasting for a second duration t2.

In one implementation of the process 240 described above, the relationship between the pixel output and the exposure duration is provided by extrapolating a linear relationship 264 between the first and second data points 262a and 262b. Because the dark current is proportional to the exposure time, the dark current per unit exposure time ($\Delta D/\Delta t$) can be approximated from the slope of the linear curve 264. That is, $$\frac{\Delta D}{\Delta t} = \frac{D2 - D1}{t2 - t1}.$$

Determination of the readout offset from the linear relationship 260, as well as other possible ways of collecting the first and second data points 262a, 262b are described below in greater detail.

In the dark current determination method described above in reference to FIGS. 6A and 6B, the pixel output includes the dark current contribution, readout offset contribution, and the spurious charge contribution. The spurious charge is included because the collected charge from the pixel needs to be read out by the shifting operation as described above. For a given pixel, however, the spurious charge contribution can be approximated as being generally constant for a given shift-out gate voltage application scheme, and not displaying significant dependence on the exposure time. The readout offset can also be approximated as being generally constant for the given pixel, and not depending on the exposure time. The change in the dark current per unit exposure time, as expressed by Equation 1, relates to a difference in two values of pixel outputs D2 and D1. Thus, the spurious charge and readout offset contributions can be subtracted out in the dark current determination.

FIGS. 7A and 7B illustrate one possible way of determining the readout offset contribution associated with readout from the output register 222. FIG. 7A illustrates a readout configuration 270 where the pixel array 220 is not shifted out, and the readout register 222 is read out (as depicted by an arrow 272) after being reset. In one embodiment, an output from such a readout includes the readout offset and does not include the spurious charge from the main array and dark current contributions associated with the main array pixels.

FIG. 7B illustrates a process 280 that performs such readout offset determination. The process 280 begins at a start state 282, and in step 284 that follows, the process 280 resets the output register 222. In step 286 that follows, the process 280 reads out the output register 222. In step 290 that follows, the process 280 determines the readout contribution resulting from the readout of the output register 222. The process 280 ends at a stop state 292.

FIG. 8A illustrates a shift-and-readout configuration 300 that is similar to what might occur during a data-acquiring process. To allow dark current determination and correction, a substantially dark environment can be provided for the pixel array 220. The pixel array 220 is shifted out as depicted by arrows 228a-228d, and following each shifting operation, the output register 222 is read out as depicted by an arrow 302. The output register 222 is typically reset prior to receiving the shift of charges from the pixel row (218 in FIG. 4).

FIG. 8B illustrates a process 310 that performs such a shift and readout operations described above in reference to FIG. 8A. The process 310 begins at a start state 312, and in step 314 that follows, the process 310 induces exposure (integration) by the pixels for an exposure time t. In step 316 that follows, the process 310 resets the output register 222 and performs the shift operation such that the output register 222 receives a row of charges. In step 320 that follows, the output register 222 is read out. Steps 316 and 320 are repeated as needed until all of the rows are shifted out and read out. In step 322 that follows, the process 310 removes the dark current and readout offset contributions from the pixel outputs to yield the spurious charge contribution. The process 310 ends at a stop state 324.

The pixel outputs provided in the foregoing manner includes the contributions from the spurious charge, dark current, and the readout offset. The dark current contribution can be approximated by the method described above in reference to FIGS. 6A and 6B. That is, the dark current associated with the exposure time t can be approximated as $(\Delta D/\Delta t)t$, where $\Delta D/\Delta t$ is expressed in Equation 1. The readout offset contribution can be approximated by the method described above in reference to FIGS. 7A and 7B. Since the readout offset contribution generally does not depend on the exposure time t, a previously determined readout offset can be used.

Figure 9B:
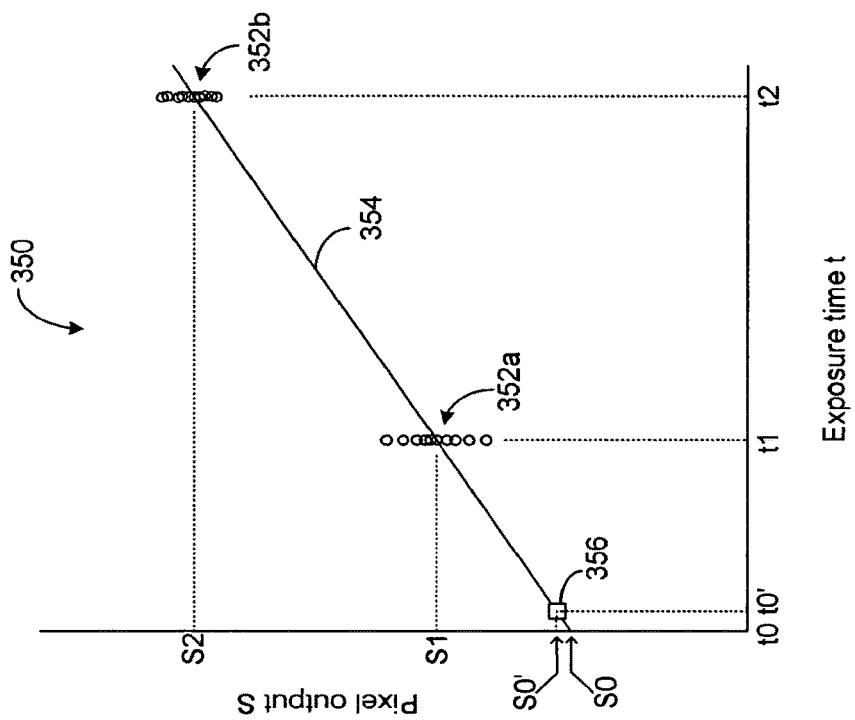
FIGS. 9A to 9D illustrate another method for determining the various noise contributions associated with the operation of the pixels according to the present teachings.
Figure 9A:
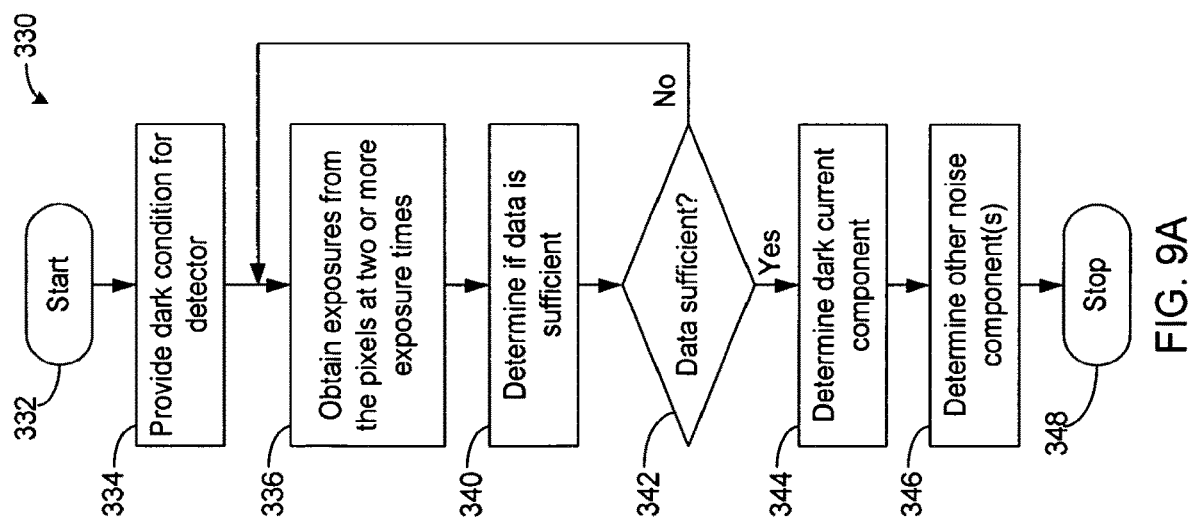

FIGS. 9A and 9B illustrate an alternate method for determining the noise contributions. As previously described in reference to FIGS. 6A and 6B, two data points provided at two different exposure times can be used to approximate the dark current. In certain configurations of the CCD, the number of charged particles generated as dark current can be relatively small. As is understood in the art, random events such as the dark current generation are subject to Poisson fluctuation, where the uncertainty in the expected number N of generated particles is approximately $1/\sqrt{N}$. Thus as an example, if an average of 100 charged particles are produced during a given exposure duration, N=100 and the uncertainty is 1/10=0.1 (10%). If the expected number N=10, the uncertainty jumps to approximately 33%. Thus, the two exemplary data points 262a and 262b of FIG. 6B can have significant uncertainties. As a result, the dark current determined can also have a significant uncertainty associated with it.

In some embodiments, a detector can include a masked region for dark current determination. Measurements from the masked region can be provided concurrently with data measurements from the main array. The dark current contribution can be determined by fitting a linear curve in a manner described below.

One possible way to mitigate the Poisson fluctuation is to perform the same measurement sufficient number of times to accurately determine the expected value of the dark current for a given exposure time. The plurality of measured dark current values then yields a Gaussian distribution whose peak (and width) can be determined in any number of known ways. Such a technique can be particularly useful for hot pixels for which approximation of dark current from the average background can be difficult.

FIG. 9A illustrates a process 330 that performs a plurality of dark current measurements to more accurately determine the expected dark current production per exposure time. The process 332 begins at a start state 332, and in step 334 that follows, the process 330 induces the detector to be subjected to a substantially dark condition. In step 336 that follows, the process 330 provides exposures from the pixels at two or more exposure times. For the purpose of description herein, two exposure times are used; however, it will again be appreciated that any number greater than two can be used without departing from the spirit of the present teachings. In step 340 that follows, the process 340 determines if the number of data points provided thus far is statistically sufficient. One way to determine such an accuracy criteria is described below in reference to FIG. 9B. In a decision step 342 that follows, the process 330 determines if the collected data is sufficient. If the collected data is not sufficient, the process 330 loops back to step 336 to collect more data. If the collected data is sufficient, the process 330 in step 344 processes the collected pixel output data to determine the dark current contribution. The process 330 in step 346 then can determine other noise contributions based on the dark current contribution. The process 330 ends in a stop state 348.

In one implementation of the process 330, the repetitive loop from the decision step 342 to step 336 can be performed so as to collect M sets of the two data points. The M sets can be provided one set (of two data points at two different exposure times) at a time. Alternatively, the first data point at the first exposure time can be provided M times, followed by M second data points at the second exposure time. In some embodiments, the latter method is less susceptible to variations in temperature.

The collection of the plurality of data points in the foregoing manner can yield a pixel output (S) dependence 350 on the exposure time (t). A cluster of first data points 352a corresponds to the exposure time t1, and a cluster of second data points 352b corresponds to the exposure time t2. The clusters of first and second data points 352a, 352b can be projected onto the "S" axis to form Gaussian distributions. Mean values of the first and second Gaussians can be determined in any number of known ways. The first mean value S1 can then correspond to the first exposure time t1, and the second mean value S2 can correspond to the second exposure time t2.

Once the first and second mean data points (t1, S1) and (t2, S2) representative of the first and second clusters of exposure data points, a linear relationship 354 can be provided. The line 354 extends through the first and second mean data points and can extend beyond so as to allow extrapolation of the pixel output S for an arbitrary exposure time t. The slope of the line 354, $\Delta S/\Delta t=(S2-S1)/(t2-t1)$, represents the dark current per unit exposure time in a similar manner as that of Equation 1 described above in reference to FIG. 6B. Thus, a dark current corresponding to a given exposure time t can be determined as $(\Delta S/\Delta t)t$. In one embodiment, hot pixels are determined and excluded from the foregoing approach.

The pixel output curve 350 described above in reference to FIG. 9B can reflect an extension of the pixel output curve 260 also described above in reference to FIG. 6B. The repetition of pixel output measurements M times in the foregoing manner provides an improved approximation of the first and second pixel outputs by mitigating the random fluctuations. It will be appreciated that similar repetitive-measurement counterpart to the readout offset determination of FIGS. 7A and 7B can be performed to provide an improved mean value of the readout offset contribution.

It will be understood that the readout offset contribution provided in the foregoing manner can be applied globally to each of the pixels. The exemplary pixel output curve 350 is representative of a selected pixel. Thus, each pixel can have associated with it information that correlates the exposure time t to that pixel's output S. Such information can include the slope and y-intercept of a linear relationship between S and t.

As previously described, the slope of the S-t relationship represents the dark current per unit exposure time. In one embodiment, they-intercept (S0 in FIG. 9B) should represent a substantially nil exposure time; thus, S0 includes the spurious charge and readout offset contributions but not the dark current contribution. Subtraction of the global readout offset value from the S0 value yields the pixel's spurious charge contribution. Many cameras, however, have a non-zero time intercept; thus, a nominal origin of the S-t curve can be greater than or less than zero. Such an origin can be determined by plotting several different curves associated with different light exposure intensities as a function of time. A crossing point or a general crossing area can represent the origin.

As illustrated in FIG. 9B, an alternative method of approximating the value of S0 (spurious charge plus readout offset values) includes providing of the given pixel's output S0' at a relatively very short exposure duration of t0'. In some embodiments, because of the relatively small value of t0', the corresponding dark current contribution can be neglected, and the value of S0' includes the spurious charge and readout offset contributions. Subtraction of the global readout offset value from the S0' value can then yield an approximation of the pixel's spurious charge contribution. In certain circumstances, such a method can be advantageous because the method does not need to depend on they-intercept extrapolated from the first and second data points 352a and b.

In some embodiments, such as in uncooled cameras, the dark current from readout is not negligible. Furthermore, when clocking, the dark current can increase particularly when operated in an MPP mode.

Figure 9C:
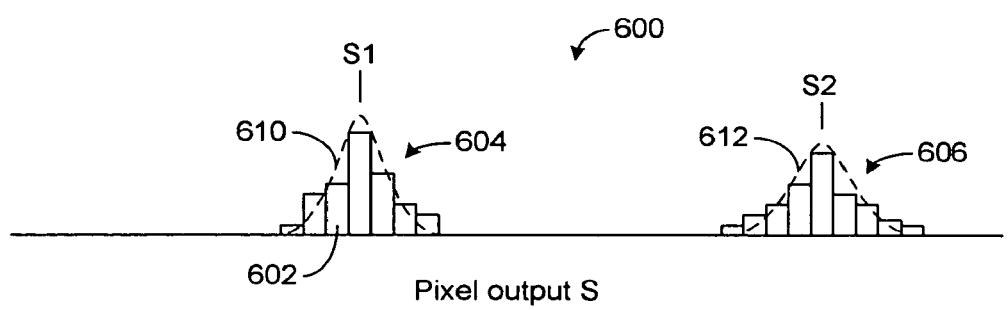

FIG. 9C illustrate how mean values of the plurality of pixel outputs can be determined so as to yield the S1 and S2 values. As previously described, projection of the pixel output data points onto the "S" axis forms a distribution of the pixel output values. Such a distribution 600 is shown in FIG. 9C, where the pixel output values are histogrammed into a plurality of appropriately sized bins 602 so as to yield first and second distributions 604 and 606 corresponding to the first and second clusters of data points.

As shown in FIG. 9C, exemplary Gaussian analyses 610 and 612 can be bit to the respective distributions 604 and 606. Gaussian analysis to fit the curve to the distributions can be performed in any number of known ways. Furthermore, one can provide mean values S1 and S2 based on the Gaussian analyses 610 and 612.

Figure 9D:
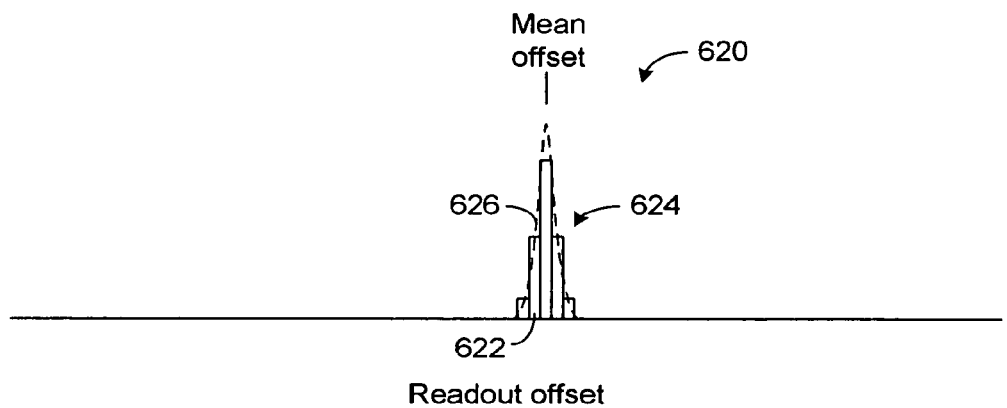

FIG. 9D illustrates a similar distribution 620 for the plurality of readout offset values provided in a manner as described above. The readout offset values can be histogrammed into a plurality of appropriately sized bins 622 so as to yield a readout offset histogram 624. The histogram 624 can then be fit with a Gaussian analysis 626 so as to allow determination of a mean offset value that can represent the readout offset contribution.

Figure 10A:
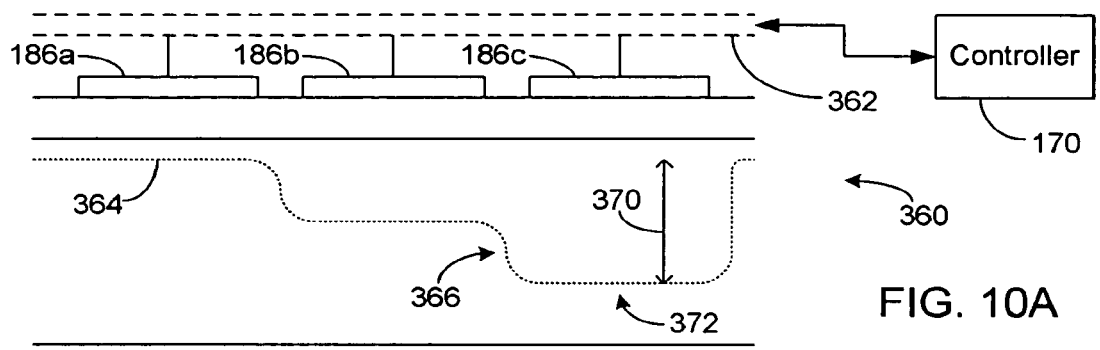
FIGS. 10A and 10B illustrate a method for characterizing the spurious charge production as a function of a gate voltage profile applied to the pixel to shift out the collected charge according to the present teachings.

FIGS. 10A and B now illustrate an exemplary method of characterizing the spurious charge contribution while varying the gate voltage profile to provide a gate voltage profile that results in a desired level of spurious charge. FIG. 10A illustrates an exemplary transfer configuration 360 having a potential profile 364. The exemplary potential profile 364 includes the well underneath the gate 186b, and an inverted region 372 underneath the gate 186c. The inverted region 372 has a potential depth 370 that is caused by the application of a gate voltage on the gate 186c. In general, the potential depth 370 determines, at least to some degree, the extent of the spurious charge production. The spurious charge production can also depend on the manner in which the potential transitions from the non-inverted to inverted configuration (i.e., transition of the gate voltage at the gate 186c). In some embodiments, the spurious charge production depends particularly on the speed of transition of the clock edge. The gate voltages typically need to be larger for a higher clock speed to maintain a similar well depth. In FIG. 10A, a potential transition region 366 depicts the transition from the collection well to the inverted region 372. The spurious charge production can also depend on how long the inverting gate voltage is applied.

In certain embodiments, the various possible manipulation of the potential profile 364 can be induced by the controller 170. The controller 170 can control the manner in which a gate voltage circuit 362 applies the various gate voltages.

Figure 10B:
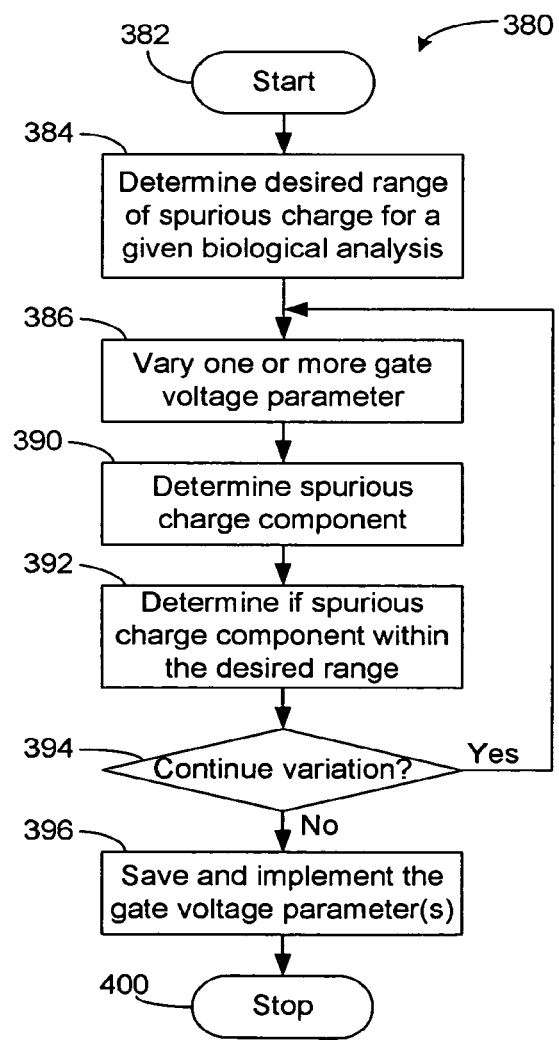

FIG. 10B illustrates an exemplary process 380 that characterizes the spurious charge for various configurations of the gate voltage application. The process 380 begins at a start state 382, and in step 384 that follows, the process 380 determines a desired range of spurious charge associated with a CCD being utilized for a given biological analysis. In step 386 that follows, the process 380 induces a variation of one or more gate voltage parameter so as to cause one or more of the potential profile change(s) described above in reference to FIG. 10A. In step 390 that follows, the process determines the spurious charge resulting from the potential profile selected. In step 392 that follows, the process 380 determines whether the spurious charge contribution is within the desired range. In a decision step 394 that follows, the process 380 determines whether the variations to the gate voltage parameter(s) should continue. If the answer is "Yes," the process 380 loops back to step 386 so as to facilitate additional gate voltage variation(s). If the answer is "No," the process 380 proceeds to step 396 where the process 380 causes the gate voltage parameter(s) to be saved and/or implemented. The process 380 ends at a stop state 400.

It will be appreciated that a gate voltage parameter "tuning" process can be used to map out a spurious charge response to one or more of the parameters. In certain embodiments, the pixels in the array can respond differently to a given set of parameters. One way to optimize the management of spurious charge is to select a set of parameters that results in the least amount of average spurious charge from all of the pixels. It will be appreciated that one can apply the gate voltage parameters determined in the foregoing manner in any number of ways to any combination of pixels without departing from the spirit of the present teachings.

Being able to characterize the pixel's noise contributions in the foregoing manner allows one to characterize the pixel array in an improved manner. FIGS. 11 to 13 now illustrate some exemplary applications that can benefit from the knowledge and availability of the pixel noise contributions. In particular, FIGS. 11A-11C illustrate how "hot" pixels can be identified in the pixel array. FIGS. 12A-12C illustrate how "cold" or "dead" pixels can be identified in the pixel array. FIGS. 13A-13C illustrate how the pixels' responses can be normalized. As is known in the art, a hot pixel can manifest an excessive dark current generation. A dead pixel can manifest a lack of output or dark current in response to an impinging signal. Pixels typically manifest some variations in the level of output for a substantially same input and under substantially same operating condition.

FIG. 11A illustrates a process 410 that determines the dark current contribution for each of the pixels in the array. The process 410 begins at a start state 412, and in step 414 that follows, the process 410 induces a dark condition to be provided for the detector. In step 416 that follows, the process 410 determines the dark current contribution for each pixel of the array. The dark current contribution determination can include removal of the spurious charge and readout offset contributions from the pixels' output in a manner described above. The process 410 ends at a stop state 420.

In certain embodiments, the process 410 can have been performed previously, and the dark current contribution for the pixels can already be stored in some database. In other embodiments, some or all of the dark current contribution determination can be performed for the purpose of hot pixel identification.

FIG. 11B illustrates a process 430 that uses the pixels' dark current information to identify the hot pixels. The process 430 begins at a start state 432, and in step 434 that follows, the process 430 determines the average value of the dark current contribution of the pixels. In certain implementations of the process 430, dark current value(s) that deviate substantially from the general cluster of "mainstream" values can be removed from the averaging process via any number of known techniques such as using a median or weighted average (averaging those values not excluded by more than a given standard deviation). In step 436 that follows, the process 430 determines a threshold value of the dark current contribution, above which a pixel can be considered to be hot. In step 440 that follows, the process 430 compares the dark current of each pixel to the threshold value to identify the hot pixels. The process 430 ends at a stop state 442.

FIG. 11C illustrates an exemplary dark current distribution 450 that depicts a plurality pixels 452 and their corresponding dark currents 454. An exemplary threshold level 456 is also indicated as a dashed line. In such an exemplary pixel array, one can see that pixel 452e manifests a dark current that exceeds the threshold level 456. Thus, the exemplary pixel 452e can be identified as a hot pixel.

In certain embodiments, the threshold level can be set at approximately three standard deviations above a noise level. Many images can then be used to insure that pixels which are not hot are not inadvertently selected. It will be appreciated, however, that the threshold level can be set at any level without departing from the spirit of the present teachings.

FIG. 12A illustrates a process 460 that determines the pixels' response to impinging light signal so as to facilitate identification of dead pixels. The process 460 begins at a start state 462, and in step 464 that follows, the process 460 induces a substantially uniform illumination condition to be provided for the detector. In step 466 that follows, the process 460 provides an exposure from the detector for a selected exposure duration. Such an exposure includes exposures from the individual pixels. In step 470 that follows, the process 460 removes the dark current, spurious charge, and readout offset contributions from each pixel's output signal to yield each pixel's corrected signal. The process 460 ends at a stop state 472.

In certain embodiments, the process 460 can have been performed previously, and the corrected signals for the pixels can already be stored in some database. In other embodiments, some or all of the corrected signal determination can be performed for the purpose of dead pixel identification.

FIG. 12B illustrates a process 480 that uses the pixels' corrected signal information to identify the dead pixels. The process 480 begins at a start state 482, and in step 484 that follows, the process 480 determines the average value of the corrected signals of the pixels. In certain implementations of the process 480, corrected signal values that deviate substantially from the general cluster of "mainstream" values can be removed from the averaging process via any number of known techniques. In step 486 that follows, the process 480 determines a threshold value of the corrected signal, below which a pixel can be considered to be dead or cold. In step 490 that follows, the process 480 compares the corrected signal of each pixel to the threshold value to identify the dead/cold pixels. The process 480 ends at a stop state 492.

FIG. 12C illustrates an exemplary corrected signal distribution 500 that depicts the plurality pixels 452 and their corresponding corrected signals 502. An exemplary threshold level 504 is also indicated as a dashed line. In such an exemplary pixel array, one can see that pixel 452g manifests an exemplary corrected signal that is substantially nil and therefore falls below the threshold level 504. Thus, the exemplary pixel 452g can be identified as a dead pixel. In certain embodiments, pixels whose corrected signals are finite but fall below the threshold 504, can be identified as cold pixels.

In certain embodiments, the threshold level can be set in a manner generally similar to that for hot pixels so as to reduce the likelihood that non-cold pixels are not inadvertently selected. It will be appreciated, however, that the threshold level can be set at any level without departing from the spirit of the present teachings.

FIG. 13A illustrates a process 510 that determines the pixels' response to a substantially uniform impinging light signal so as to facilitate the comparison of the pixels' response. This signal noise contribution associated with how a pixel responds to substantially uniform light is known as photo response non-uniformity. The process 510 begins at a start state 512, and in step 514 that follows, the process 510 induces a substantially uniform illumination condition to be provided for the detector. In step 516 that follows, the process 510 provides an exposure from the detector for a relatively long exposure duration. Such an exposure includes exposures from the individual pixels. In step 520 that follows, the process 510 removes the dark current, spurious charge, and readout offset contributions from each pixel's output signal to yield each pixel's corrected signal. The process 510 ends at a stop state 522.

In certain embodiments, the process 510 can have been performed previously, and the corrected signals for the pixels can already be stored in some database. In other embodiments, some or all of the corrected signal determination can be performed for the purpose of pixel response analysis described below.

FIG. 13B illustrates a process 530 that uses the pixels' corrected signal information to compare the pixels' responses to a substantially uniform input. The process 530 begins at a start state 532, and in step 534 that follows, the process 530 determines the average value of the corrected signals of the pixels that are not hot or dead. In step 536 that follows, the process 530 determines a normalization factor for each pixel based on the average value of the corrected signals. In step 540 that follows, the process 530 saves the normalization factors for the pixels to allow application during subsequent measurement of signals. The process 530 ends at a stop state 542.

FIG. 13C illustrates an exemplary corrected signal distribution 550 that depicts the plurality pixels 452 and their corresponding corrected signals 552. An exemplary average value 554 of the corrected signals is also indicated as a dashed line. In such an exemplary pixel array, one can see that the exemplary hot pixel 452e is identified as being hot, and its output signal is removed from the distribution. Furthermore, the exemplary dead pixel 452g is identified as a being dead. The remaining exemplary pixels 452a-452d, 452f, and 452h-452j have associated with them normalization factors. For example, the pixel 452a has an exemplary normalization factor of 1.2, meaning that in this particular example of normalization scheme, the pixel's output is approximately 20% above the average response level. Thus, to normalize a subsequent corrected signal from pixel 452a that corrected signal can be divided by the factor 1.2 thereby reducing the value of the signal by approximately 20%. It will be appreciated that any number of normalization schemes can be utilized to normalize the pixels' response without departing from the spirit of the present teachings.

Figure 14:
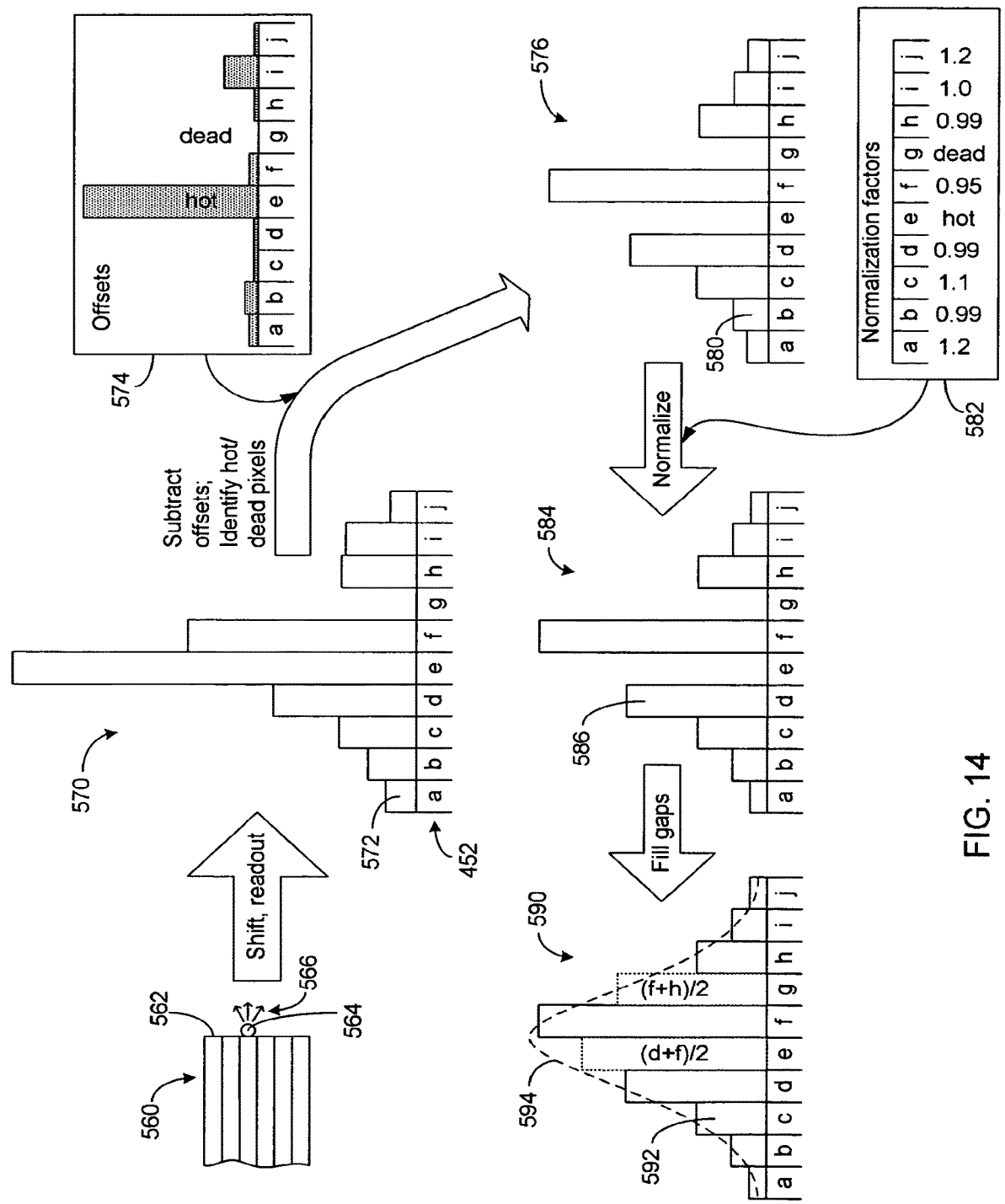
FIG. 14 illustrates an application of the pixels' noise contributions characterization to correct a raw signal output from a CCD according to the present teachings.

FIG. 14 now illustrates an exemplary processing of signals to correct for the noise contributions described above, thereby improving the quality of the measurement. An exemplary fiber array 560 having a plurality of tips 562 is used for descriptive purpose. It will be appreciated, however, that the correction process can be applied to any other biological analysis systems without departing from the spirit of the present teachings.

An exemplary cluster 564 of fragments is depicted as being attached to one of the fiber tips 562. The fragments 564 are tagged with fluorescing labels that emit detectable signal 566 whose intensity and spatial distribution are indicative of the type and concentration of the fragment in the sample. The signal 566 impinges on the detector, and the pixels are read out by shifting and register readout operations so as to yield a raw data 570 including output signals 572 corresponding to the pixels 452.

The raw data 570 can then be corrected for the noise contributions as described above. An offset information 574 is depicted as including the net correction value which includes the readout offset, spurious charge, and dark current contributions. A correction value is associated with each pixel, and preferably the dark current contribution accounts for the exposure duration of the shot of the sample signal 566. The offset information 574 can also identify the hot and/or dead pixels determined as described above. Although the offset information 574 is depicted as a single entity in FIG. 14, it will be appreciated that the noise contributions information as well as the hot/dead pixel list can be stored in some form of a database in any number of ways.

Removal of the offset values from the pixels' raw data yields a corrected data 576 including corrected signals 580 corresponding to the pixels 452. The corrected data 576 is also depicted as having signals (or lack of signals) associated with the hot and dead pixels removed from further processing.

The corrected data 576 can be normalized by incorporating the normalization factors as depicted by a normalization factor information 582. The information 582 can be stored in some form of a database in a similar manner as that of the offset information 574 described above. Normalization of the corrected data 576 yields a normalized data 584 including normalized signals 586 corresponding to the pixels 452.

At this stage, the normalized data 584 is a more accurate representation of the detected signal 566 than that of the raw data 570 or the corrected data 576. In certain embodiments, the gaps resulting from the hot and/or dead pixels can be accounted for in any number of ways. For example, the hot pixel 452e can be assigned an approximated value by taking an average of the signal values of the two neighboring pixels. Thus, the approximated value e for pixel 452e can be expressed as (d+f)/2. Similarly, the dead pixel 452g can be assigned an approximated value g=(f+h)/2. Similarly in a 2-dimensional image, eight surrounding pixels can be averaged to approximate a value for the hot/dead pixel.

The correction, normalization, and possibly gap filling, as described above, yields analysis data 590 that is representative of the sample signal 566. The analysis data 590 includes analysis signals 592 corresponding to the pixels 452. The analysis data 590 can further be characterized by a fit curve 594 so as to allow parameterizing the data 590 in terms of spatial distribution and/or the intensity of the sample signal 566.

It will be appreciated that the various noise contributions associated with the operation of the CCD can be determined, stored, and applied in any combination. The application of the noise contributions can include the correction of the measured data as described above to yield an improved representation of the biological sample being analyzed. The application of the noise contribution can also include characterization of the various biological analysis devices, some of which were exemplified above, for the purpose of machine diagnostics and/or calibration. Furthermore, the various noise contributions correction parameters can be provided during various calibration stages of the devices, in conjunction with the sample measurements, or any combination thereof, without departing from the spirit of the present teachings.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated can be made by those skilled in the art without departing from the scope of the present invention. Consequently, the scope of the invention should not be limited to the foregoing description, but should be defined by the appended claims.

What is claimed:

1. A method comprising:
providing a detector comprising a plurality of pixels that are capable of forming an optical image of fluorescent light emitted from a biological sample, the detector being a CCD detector or a CMOS detector;
using the detector to detect a first fluorescent signal from a biological sample;
generating a first electronic signal that corresponds to said first fluorescent signal;
characterizing a signal noise component of the first electronic signal as a characterized signal noise component comprising a dark current contribution;
manipulating the detector to reduce signal noise by controlling a gate voltage of a third electronic signal based on the signal noise component, and to form a manipulated detector;
using the manipulated detector to detect a second fluorescent signal from the biological sample; and
using the manipulated detector to generate a second electronic signal.

2. The method of claim 1, wherein the characterizing the signal noise component of the first electronic signal further comprises characterizing the signal noise component as at least one of a spurious charge contribution and a readout offset contribution.

3. The method of claim 2, further comprising:
resetting a readout register of the detector;
receiving an output of the readout register; and
determining the readout offset contribution from the received output.

4. The method of claim 2, wherein characterizing the spurious charge contribution comprises analyzing a transfer of a collected charge of the plurality of pixels.

5. The method of claim 2, wherein the spurious charge contribution depends on a gate voltage profile applied to a region about the pixel.

6. The method of claim 1, wherein manipulating the detector to reduce signal noise is further based upon a readout time and an integration time.

7. An imaging system for analysis of a biological sample, comprising:
a detector comprising a plurality of pixels, the detector being a CCD detector or a CMOS detector;
a readout component configured to read an output signal from each of the plurality of pixels;
a controller configured to induce a substantially uniform illumination condition to the detector and provide an exposure from each of the plurality of pixels, for a selected exposure duration; and
a processor programmed to:
(i) remove signal noise from the output signal of each pixel to yield a corrected signal for each pixel,
(ii) identify at least one hot pixel and at least one dead pixel,
(iii) determine an average value of the corrected signals from pixels that are not identified as hot pixels or dead pixels,
(iv) determine a respective normalization factor for each of the plurality of pixels,
(v) save the normalization factor for each pixel, and
(vi) determine a gate voltage about a pixel based on the signal noise.

8. The imaging system of claim 7, further comprising a data structure containing pixel noise data for at least some of the plurality of pixels and corrected signals data, the corrected signals data comprising a comparison of a response of the plurality of pixels to a uniform input.

9. The imaging system of claim 8, wherein the processor is configured to adjust measurement signals produced by the detector based at least in part on the pixel noise data and the corrected signals data.

10. The imaging system of claim 8, wherein the data structure further comprises one or more of:
an average of the corrected signals data; or
the normalization factor for at least some of the pixels of the plurality of pixels, the normalization factor being based at least in part on the average.

11. The imaging system of claim 7, wherein the signal noise comprises at least one of a dark current contribution, a readout offset contribution, and a spurious charge contribution.

12. The imaging system of claim 7, wherein the controller is configured to receive signals from the processor and control gate voltages of the plurality of pixels based on the received signals.

13. A method for analysis of a biological sample, comprising:
providing a imaging system comprising:
a detector comprising a plurality of pixels;
a readout component configured to read an output signal from each of the plurality of pixels;
illuminating the detector with a substantially uniform illumination condition;
while illuminating the detector, exposing each of the plurality of pixels for a selected exposure duration;
producing an output signal from each of the plurality of pixels;
removing signal noise from the output signal of each of the plurality of pixels to yield a corrected signal for each pixel;
determining an average value of the corrected signals;
determining a threshold value below which a pixel is identified to be a dead pixel;
comparing the corrected signal of each pixel to the threshold value; and
identifying at least one of one or more dead pixel from the plurality of pixels or one or more hot pixel from the plurality of pixels.

* * * * *